(12) United States Patent
Irie et al.

(10) Patent No.: US 6,288,035 B1
(45) Date of Patent: *Sep. 11, 2001

(54) METHOD OF TREATING CANCER WITH A 43 KD HUMAN CANCER ANTIGEN

(75) Inventors: Reiko F. Irie, Pacific Palisades, CA (US); Takanori Oka, Hiroshima (JP)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,410

(22) Filed: Feb. 15, 2000

Related U.S. Application Data

(62) Division of application No. 09/247,146, filed on Feb. 9, 1999, which is a division of application No. 08/602,864, filed as application No. PCT/US94/09798 on Aug. 30, 1994, now Pat. No. 5,869,636, which is a continuation-in-part of application No. 08/190,801, filed on Feb. 1, 1994, now Pat. No. 5,705,179, which is a continuation-in-part of application No. 08/115,170, filed on Aug. 31, 1993, now abandoned.

(51) Int. Cl.[7] .............................. A61K 38/00; C07H 21/04
(52) U.S. Cl. ........................ 514/12; 536/23.5; 530/300; 530/325; 530/326; 530/327; 530/328; 530/330; 424/184.1
(58) Field of Search .............................. 514/12; 536/23.5; 530/300, 325, 326, 327, 328, 330; 424/184.1

(56) References Cited

U.S. PATENT DOCUMENTS

| | | | |
|---|---|---|---|
| 4,806,628 | 2/1989 | Albino et al. | 530/387 |
| 5,030,621 | 7/1991 | Bystryn | 514/21 |
| 5,137,806 | 8/1992 | LeMaistre et al. | 435/6 |
| 5,192,537 | 3/1993 | Osband | 424/85.2 |
| 5,194,384 | 3/1993 | Bystryn | 435/240.2 |
| 5,362,631 | 11/1994 | Calabretta | 435/69.5 |
| 5,705,179 * | 1/1998 | Fulton, Jr. | 424/423 |
| 5,869,636 * | 2/1999 | Irie et al. | 536/23.5 |
| 6,077,950 * | 6/2000 | Irie et al. | 536/23.5 |

OTHER PUBLICATIONS

Amagia et al., "Autoantibodies against a novel epithelial cadherin in pemphigus vulgaries, a disease of cell adhesion," *Cell*, 67:869–877, 1991, month not available per examiners request.

Brown et al., "Human melanoma–associated antigen p97 is structurally and functionally related to transferrin," *Nature*, 296:171–173, 1982, month not available per examiners request.

Bystryn et al., "Identification of immunogenic human melanoma antigens in a polyvalent melanoma vaccine," *Cancer Res.*, 52:5948–5953, 1992, month not available per examiners request.

(List continued on next page.)

*Primary Examiner*—Louise N. Leary
(74) *Attorney, Agent, or Firm*—Fulbright & Jaworski LLP

(57) ABSTRACT

A tumor associated protein has been discovered to exhibit immunoreactivity to human monoclonal antibody L92. A ten amino acid peptide segment of the protein and a fourteen amino acid peptide which contains the ten amino acid peptide has also been isolated and exhibits immunoreactivity to the same antibody. Using truncated fusion proteins, the minimum recognition site for antibody binding was determined to be four amino acids. Also disclosed are polypeptide compositions against human tumors that includes the polypeptides or protein of the present disclosure, as well as antibodies reactive with these polypeptides that may be employed directly for treatment or diagnosis. A certain embodiment of the present invention is also the DNA sequence encoding the ten amino acid peptide and the DNA encoding the fourteen amino acid peptide which also exhibits immunoreactivity to human monoclonal antibody L92 and cytotoxic T cells.

45 Claims, 14 Drawing Sheets

OTHER PUBLICATIONS

Figure 2:
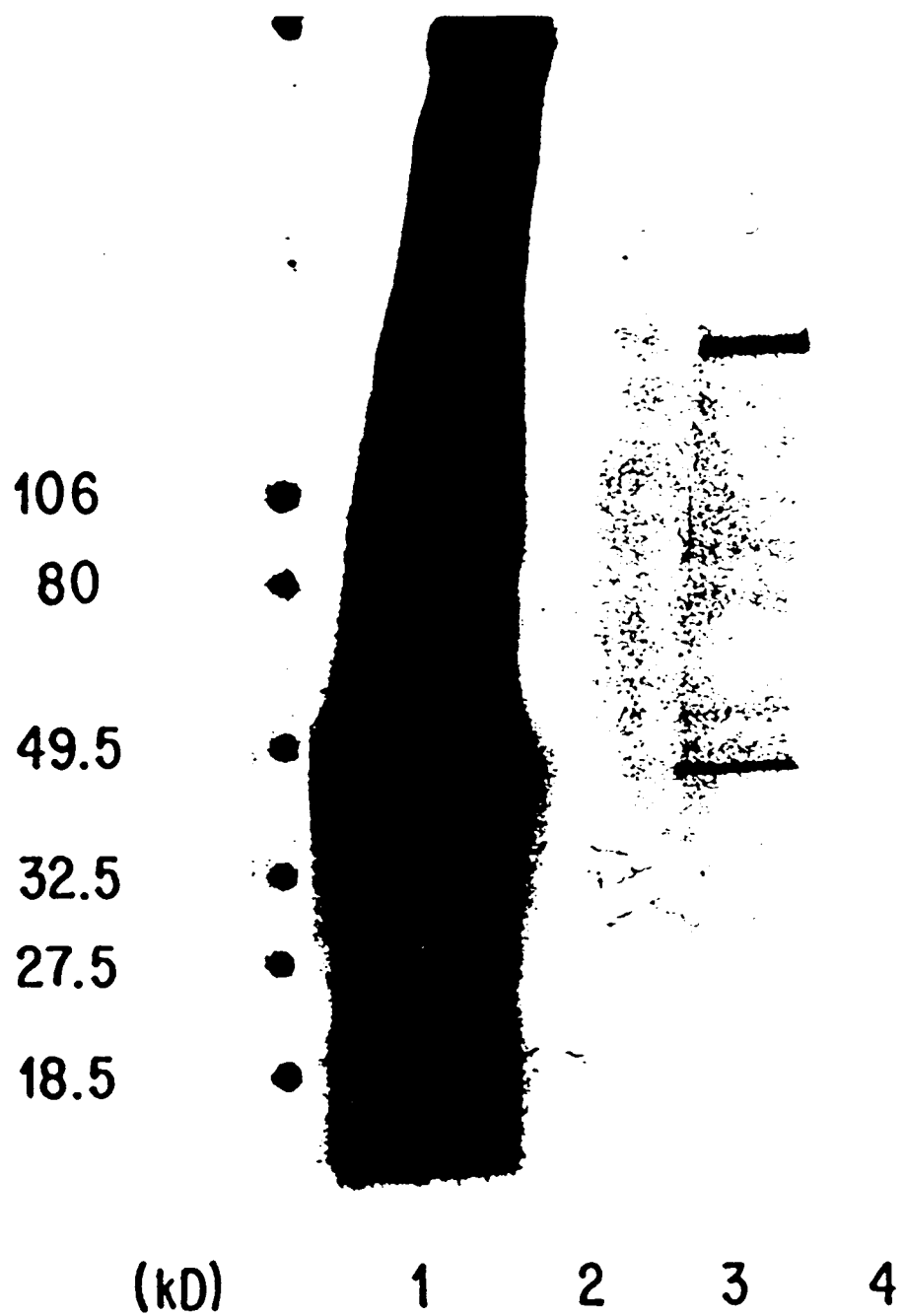

Carey et al., "AU cell–surface antigen of human malignant melanoma: solubilization and partial characterization," *Proc. Natl. Acad. Sci. USA*, 76(6):2898–2902, 1979, month not available per examiners request.

Dropcho et al., "Cloning of a brain protein identified by autoantibodies from a patient with paraneoplastic cerebellar degeneration," *Proc. Natl. Acad. Sci. USA*, 84:4552–4556, 1987, month not available per examiners request.

Erb et al., "Antigens recognized by two human monoclonal IgM anticolon cancer antibodies, 16.88 and C–OU1 (B9165)," *Hum. Antibod. Hybridomas*, 2:215–221, 1991, month not available per examiners request.

Fontan et al., "Macrophage–induced cytotoxicity and antimetastic activity of a 43–kDa human urinary protein against the Lewis tumor," *Int. J. Cancer*, 53:131–136, 1993, month not available per examiners request.

Glasky et al., "Adenocarcinoma–reactive human monoclonal antibody MS2B6 defines an antigen in simple glandular epithelium," *Hum. Antibod. Hybridomas*, 3:114–122, 1992, month not available per examiners request.

Hayashibe et al., "Cloning and in vitro expression of a melanoma–associated antigen immunogenic in patients with melanoma," *J. Immunol.*, 14(3):1098–1104, 1991, month not available per examiners request.

Kikumoto et al., "A human monoclonal antibody identified an immunoreactive tetrapeptide sequence (KYQI) in 43kD protein of human melanoma," Proceedings of the 85th Meeting of the American Association for Cancer Research, Apr. 10–13, 1994, 35:498, 1994, Abstract No. 2971, month not available per examiners request.

Kusama et al., "Characterization of syngeneic antiidiotypic monoclonal antibodies to murine Anti–human high molecular weight melanoma–associated antigen monoclonal antibodies," *J. Immunol*, 143(11):3844–3852, 1989, month not available per examiners request.

Mattes et al., "Class 1 (Unique) tumor antigens of human melanoma: partial purification and characterization of the FD antigen and analysis of a mouse polyclonal antiserum," *Cancer Res.*, 47–6614–6619, 1987, month not available per examiners request.

Morioka et al., A decapeptide recognized by cytotoxic T lymphocytes on a human melanoma, Proceedings of the 85th Meeting of the American Association for Cancer Research, Apr. 10–13, 1994, 35:513, 1994, Abstract No. 3059.

Morton et al., "Prolongation of survival in metastatic melanoma after active specific immunotherapy with a new polyvalent melanoma vaccine," *Ann. Surg.*, 216(4):463–482, 1992, month not available per examiners request.

Oka et al., "Human monoclonal antibody identified an immunoreactive tetrapeptide sequence (Lys–Tyr–Gln–Ile) in Mr 43,000 protein of human melanoma," *Cancer Research*, 54(13):3511–3515, 1994, month not available per examiners request.

PCT Search Report mailed Jan. 20, 1995.

Rizzuto, et al., "Nucleotide sequence of the cDNA encoding subunit Vlle of cytochrome c oxidase from the slime mold dictyosielium discoideum," *Nucleic Acids Res.*, 18:6711, 1990, month not available per examiners request.

Rosenberg et al., "A new approach to the adoptive immunotherapy of cancer with tumor–infiltrating lymphocytes," *Science*, 233:1318–1321, 1986, month not available per examiners request.

Smith et al., Human monoclonal antibody recognizing an antigen associated with ovarian and other adenocarcinomas, *Am J Obstet Gynecol*, 166(2):634–45, 1992, month not available per examiners request.

Szabo et al., "HuD, a paraneoplastic encephalomyelitis antigen, contains RNA–binding domains and is homologous to elav and sex–lethal," *Cell*, 67:325–333, 1991, month not available per examiners request.

Tan, "Autoantibodies in pathology and cell biology," *Cell*, 67:841–842, 1991, month not available per examiners request.

* cited by examiner

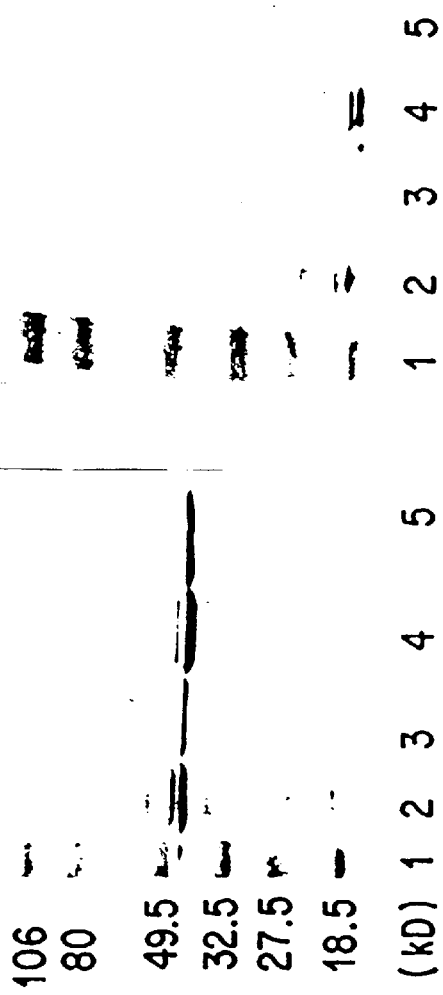

β-galactosidase — ┌ sp  Ser Arg Pro Gln Asp Leu Thr Met Lys Tyr Gln Ile Phe Stop
                  │ GAT TCG CGC CCG CAG GAT CTG ACT ATG AAA TAT CAG ATC TTT TAA
                  └ CTA AGC GCG GGC GTC CTA GAC TGA TAC TTT ATA GAC TAG AAA ATT

FIG. 4

FIG.8A
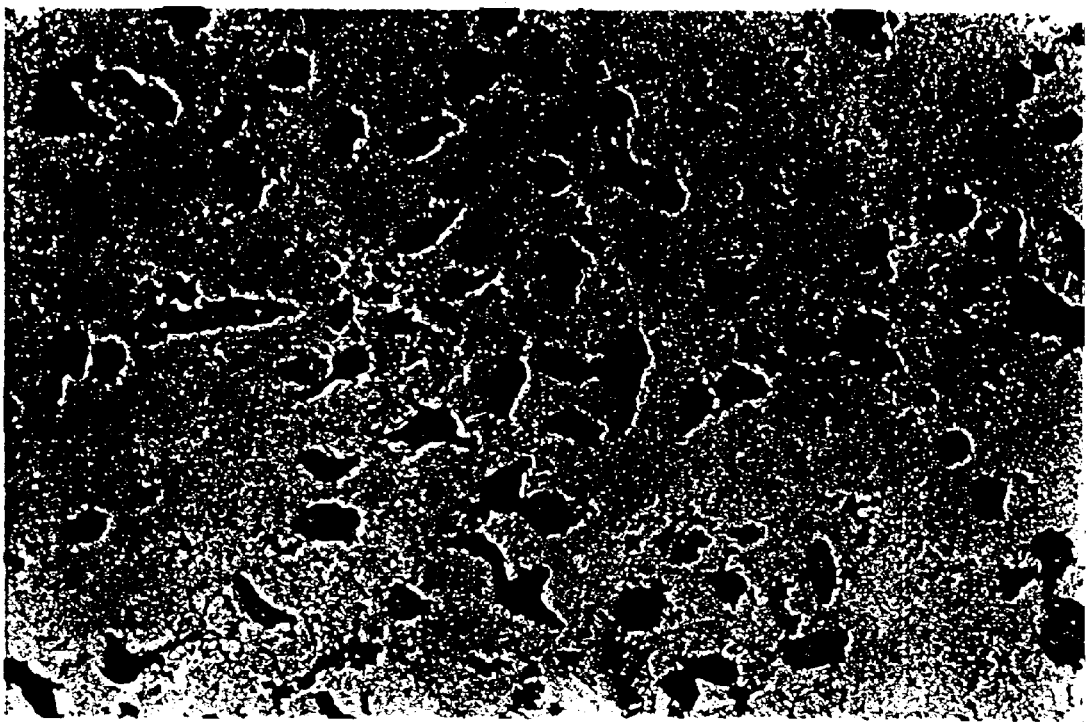
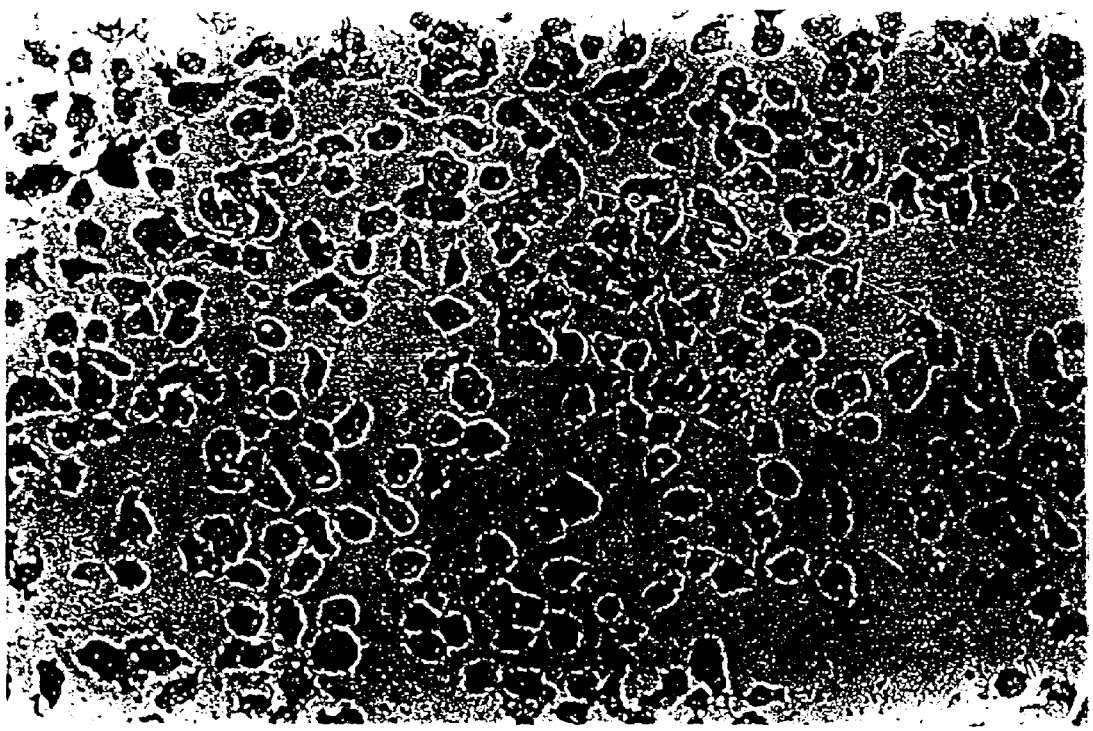
FIG.8B

Patient B

* autologous target

Patient D

* autologous target

METHOD OF TREATING CANCER WITH A 43 KD HUMAN CANCER ANTIGEN

This present application is a divisional of co-pending application U.S. Ser. No. 09/247,146, filed Feb. 9, 1999, which was a divisional of U.S. Ser. No. 08/602,864, filed Feb. 28, 1996, issued Feb. 9, 1999 as U.S. Pat. No. 5,869,636; which was a U.S. nationalization of international application PCT/USA94/09798, filed Aug. 30, 1994, which was a continuation-in-part of application U.S. Ser. No. 08/190,801, filed Feb. 1, 1994 and issued Jan. 6, 1998 as U.S. Pat. No. 5,705,179, which was a continuation in part of U.S. Ser. No. 08/115,170, filed Aug. 31, 1993, now abandoned.

The government own rights in the present invention pursuant to grant numbers CA 12582, CA 56059 and CA 30647 from The National Institutes of Health.

The present invention relates generally to the field of immunotherapy based on the identification and isolation of human tumor antigens. In particular embodiments, the invention also relates to the use of human monoclonal antibodies to isolate the epitopic sequence of a tumor-associated antigen. Further embodiments relate to synthetic peptides derived from tumor-associated proteins and their uses for therapy, diagnosis and prognosis of human cancer.

The ideal tumor vaccine is one that induces anti-tumor immunity without adverse effects. Ideally, such a vaccine would be stable, inexpensive to produce and easily administered. Early attempts with whole cell vaccines or cellular extracts, have improved the survival of cancer patients significantly. However, problems still exist with the production, storage and delivery of the vaccines. For example, there still exists the possibility of contamination by cellular molecules that may induce side effects in patients.

Because of these problems, synthetic or recombinant antigens are contemplated to be more effective vaccines, provided the antigen delivery system, carrier molecules, and adjuvants are optimized for the induction of specific anti-tumor immunity. What is needed is the identification and characterization of tumor antigens that play important roles in tumor destruction in vivo, in particular those capable of inducing T-cell immunity in humans.

Because elevated titers of autoantibodies are known to be present in hosts with various autoimmune diseases, neuropathological diseases and cancers, they have been used to screen cDNA clones from expression libraries in order to discover pathogenic antigens of such diseases (Tan E M, 1991; Amagai M et al, 1991; Dropcho E J et al., 1987; Szabo A et al., 1991; Hayashibe K et al., 1991). The difficulties of using this approach to identify human tumor associated antigens (TAA) include the unavailability of high titer human anti-TAA antibodies and the interference of serum antibodies unrelated to TAA.

Melanoma associated antigens (AU and FD) unique to autologous melanoma cells have been detected using autologous sera (Carey T E et al., 1979). The FD antigen is a 90 kD cell-surface glycoprotein. The antigenic determinant is present on an ion-binding protein with amino acid homology to transferrin (Real F X et al., 1984). The same molecule was identified by murine monoclonal antibodies developed against the human melanoma-associated antigen p97 (Brown J P et al, 1982). Although the sequence of p97 is known, the sequence of the unique FD epitope has not yet been determined. The Hellstrom laboratory has investigated the 97,000 MW glycoprotein antigen, p97, that is predominantly expressed by human melanoma cells (Woodbury R G et al., 1980; Brown J P et al., 1981). The p97 gene has been inserted into a recombinant vaccinia virus and has induced strong anti-tumor immunity against mouse melanoma cells transfected to express the p97 antigen (Brown J P et al., 1982). A clinical trial with this vaccine is ongoing by this group (Hellstrom I et al., 1992).

Vlock and colleagues used autologous melanoma sera after dissociating serum immune complexes via acidic treatment and found an antigenic 66 kD acidic glycoprotein (Vlock D R et al., 1988). Subsequent epitope analysis has shown that the carbohydrate moiety of the glycoprotein represents its antigenic determinant. The sequence of the core protein has not been reported.

Allogeneic polyclonal sera from melanoma patients have also been used to identify immunogenic melanoma associated antigens. These antigens are shared by more than one melanoma. Bystryn and colleagues detected immunogenic melanoma associated antigens (200+, 150, 110, 75, and 38 kD) using sera from patients who received immunotherapy with melanoma cell supernatant (Li J et al., 1990).

Gupta and associates have defined a urinary tumor associated antigen (UTAA), which is a glycoprotein antigen originally found in the urine of melanoma patients and also found on the melanoma cell surface, including the M14 cell line. The UTAA is comprised of several subunits that are linked together by disulfide bonds. The total molecular weight is approximately 300 kD, with immunogenic subunits of 45 kD, 65 kD, 90 kD, 120 kD and 150 kD (Euhus D M et al., 1990).

Ferrone and colleagues used pooled sera from melanoma patients to identify a 50 kD glycoprotein antigen (D-1) in melanoma (Hayashibe K et al., 1991). Using cDNA libraries of a melanoma cell line, the immunoreactive clone was isolated and sequenced. The successful cloning was possible after extensive absorption of non-specific antibodies with *E. coli* proteins and blocking of cDNA plaques on nitrocellulose with IgG isolated from the pooled sera of healthy donors. While the exact tumor specificity of this protein (D-1) is not known, northern blot hybridization has shown that peripheral blood lymphocytes (PBL) and normal fibroblasts do not express this antigen.

Several other studies have identified protein molecules from other human cancer cells that migrate at or around the 43 kD position in SDS-PAGE Western blot analysis. These studies have used murine or human monoclonal antibodies. HGP43 is a human glycoprotein of 43 kDa, which was identified by murine monoclonal antibody and was originally reported as a protective antibody against lethal *Listeria monocytogenes* infection in mice (Fontan E et al, 1992). HGP43 is detected in the urine of healthy, normal individuals as well as in cancer patients. HGP43 has also been shown to stimulate mouse monocytes to induce cytotoxicity against the Lewis lung tumor (Fontan E et al., 1993). The amino acid sequence from HGP43 that is reactive to the monoclonal antibody has not been reported.

The human monoclonal antibodies 16.88 and C-OU 1 react with another 43 kD protein molecule in human cancer cells (Erb K et al., 1991). The antigen is most strongly expressed in melanoma and less strongly in colon cancer cells. The amino acid sequence of this protein is partially known and exhibits about 70% identity with cytokeratin 18.

Another HuMAb, MS2B6, has been used to detect a cytoplasmic antigen present at high density in ovarian carcinoma and is less prevalent in a variety of human cancers and in certain types of normal tissues (Smith L H et al., 1992). On SDS-PAGE Western blot analysis, MS2B6 reacted to proteins with a broad range of molecular weights, 33–44 kD and 60 kD. Competitive inhibition studies have shown no crossreactivity between the antigen identified with MS2B6 and the cytokeratin identified with HuMAbs 16.88 and C-OU 1.

Another approach to developing anti-tumor vaccines is the development of anti-idiotype vaccines. In this method, MAbs are developed against an antigen of interest. These antibodies are then used to screen an epitope library to find a peptide that mimics the target antigen. This anti-id epitope is then used as a vaccine. This is particularly important in developing antibodies to glycosidic antigens which cannot be easily synthesized. Dr. Ferrone's laboratory has pursued an investigation of anti-id vaccines mimicking high molecular weight melanoma associated antigens (HMW-MAAs) for the active specific immunotherapy of melanoma (Kusama M et al., 1989). The HMW-MAAs are expressed in high density by melanoma cells, but have a restricted distribution on normal tissues (Reisfeld R A and Cheresh D A, 1987). Anti-ids mimicking HMW-MAAs were developed using syngeneic murine monoclonal antibodies to MAAs as immunogens. When these anti-id vaccines were injected in mice and rabbits, specific immune responses were demonstrate (Kusama M et al., 1989; Challopadhyay P et al., 1991). Injection of these vaccines into patients during a Phase I clinical trial has shown that the anti-id vaccine is safe and has induced clinical responses in patients with melanoma, including 2 complete remissions (Mittelman A et al., 1992). However, the high anti-tumor antibody or T-cell responses observed in animal models have not been replicated in clinical trials. The weak immune responses seen in patients by immunization with these antigens may reflect, therefore, the fact that these antigens may be partially tolerated under normal immunologic conditions in humans.

Therefore, there still exists an immediate need for an anti-tumor immunotherapy. An effective vaccine would comprise tumor antigens that can induce antibody and/or T cell immune responses in humans.

The present invention seeks to overcome these and other drawbacks inherent in the prior art by identifying and isolating protein antigens that are highly immunogenic in humans. These antigens are then used in vaccines to promote specific anti-tumor responses.

An important embodiment of the present invention is a purified polypeptide which has been found to be immunoreactive with HuMAb L92. More particularly, this embodiment of the invention is a purified polypeptide that includes the 4 amino acid segment KYQI (SEQ ID NO:8), or the purified polypeptide that includes the 9 amino acid segment QDLTMKYQI (SEQ ID NO:9) or even a purified polypeptide that includes the 10 amino acid segment QDLTMKYQIF (SEQ ID NO:1). The purified polypeptide of the invention may be further defined as including the sequences delineated as SEQ ID NOS:1, 8 and 9 and comprising a molecular mass of about 43 kDa as defined by the mobility of the protein through a denaturing polyacrylamide gel relative to proteins of known molecular mass.

The term "purified polypeptide" as used herein, is intended to refer to a polypeptide composition, isolatable from other tumor cell associated proteins, wherein the polypeptide is purified to any degree relative to its naturally-obtainable state, i.e., in his case, relative to its purity within a tumor cell extract. A purified polypeptide therefore also refers to a polypeptide, free from the environment in which it may naturally occur in intact cells.

In certain embodiments, "purified" will refer to a polypeptide composition which has been subjected to fractionation to remove various non-protein components such as other cell components. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

In certain other embodiments, the purified polypeptide will be chemically synthesized by solid phase synthesis and purified away from the other products of the chemical reactions by HPLC for example. Alternatively, the polypeptide may be produced by the overexpression of a DNA sequence included in a vector in a recombinant cell. In this method of producing the polypeptide, purification would be accomplished by any appropriate technique mentioned in the preceding paragraph.

It is understood that other peptide segments of the 43 kDa protein may also be immunoreactive with HuMAb L92. For example, it is known that antigenic determinants are sometimes discontinuous and therefore another peptide segment of the same 43 kDa protein, may also be immunoreactive with the HuMAb L92. All such peptide segments either continuous or discontinuous, and even including the full length protein which is recognized by HuMAb L92 are understood to be encompassed by the present invention and to lie within the scope of the present claims. For example, a purified polypeptide which includes the sequences designated herein as SEQ ID NOS: 1, 8 or 9 and having a length of less than 100 amino acids, or having a length of less than 50 amino acids, or having a length of less than 25 amino acids or even defined as having a length of 10 amino acids or less would also be included within the scope of the present claimed invention.

It is also understood that a protein or polypeptide segment of the present invention may also be fused, generally by genetic techniques well known to those of skill in the art, to a carrier protein and that such a protein-protein or protein-peptide fusion which exhibits immunoreactivity with HuMAb L92 is also encompassed by the present invention. For example, a polypeptide that contains any of the amino acid sequences designated herein as SEQ ID NOS:1, 8 or 9 and further including the amino acid sequences of β-galactosidase or glutathione-S-transferase, for example would also be an embodiment of the present invention. It is understood that these carrier protein sequences are mentioned by way of example only and that other known carrier protein sequences such as keyhole limpet hemocyanin (KLH), bovine serum albumin (BSA), other albumins such as ovalbumin, mouse serum albumin or rabbit serum albumin or any other suitable protein sequence may also be included as embodiments of the present invention. It is further understood that the use of the term "protein" does not limit the invention to polypeptides or peptides of any particular size. Peptides from as small as several amino acids in length to proteins of any size as well as protein-peptide fusions are encompassed by the present invention, so long as the protein or peptide is antigenic and/or exhibits low immunogenicity.

In a general sense, the proteins or polypeptides of the present invention may be defined as being associated with, or derived from human tumor cells. Even more particularly, the proteins and peptides of the present invention may be defined as a protein of $M_r$ of about 43 kDa and associated with human tumor cells which is immunoreactive with HuMAb L92; any polypeptide fragments of said 43 kDa protein; protein fusions or peptide-protein fusions comprising any part of the said 43 kDa protein; and even more particularly, a protein-peptide fusion capable of immunoreactivity with HuMAb L92 in which a polypeptide, preferably one of those peptide sequences designated as SEQ ID NOS:1,8 or 9 is fused with β-galactosidase or GST. It is understood that using the techniques of recombinant DNA, any portion of the sequence of the 43 kDa protein including the entire coding sequence and any promoters, enhancers, poly A splice site, ribsome binding site or other transcription or translation control sequences may be inserted into a foreign DNA sequence and expressed in order to obtain a protein with immunoreactivity to HuMAb L192 and that any such use of the genetic and/or amino acid sequences of the 43 kDa protein are encompassed by the present claimed invention.

It is further understood that the amino acid sequence or underlying genetic sequence of the protein of the present disclosure may be altered by for example, site directed mutagenesis, or by any other means and a protein may be obtained thereby which retains its biological utility and antigenicity. It is also understood that such altered proteins may not retain the biological activity, or they may possess altered or enhanced biological function or antigenicity and all such altered proteins are encompassed by the present invention.

In a further embodiment, the present invention relates to a recombinant cell line capable of producing the proteins, polypeptides and/or protein-protein or protein-polypeptide fusions discussed in the preceding paragraphs. The said cell line may preferably be a bacterial cell line, such as an $E.\ coli$ cell line which contains within the cells a plasmid or viral vector comprising a DNA segment encoding the protein, peptide or fusion of the present invention and the control elements necessary for the replication of the vector and for expression of the polypeptide, protein or fusion. It is understood that the cell line may also be another bacterial cell, or a yeast, plant, animal or even a human cell line. The selection of the appropriate cell line and a compatible vector are well known to those of skill in the art and all such cell lines and vectors fall within the scope of the present invention. It is also understood that the expression of the gene encoding the protein may be under the control of an inducible promoter, for example the lac promoter and that expression may be controlled by exogenously applied inducers. Most preferably, the peptides designated herein as SEQ ID NOS:1, 8 and 9 are fused to β-galactosidase, under the control of the lac promoter and expressed in an $E.\ coli$ cell line.

As used herein, the term "recombinant" cell line is intended to refer to a cell into which a recombinant gene, such as a gene encoding a polypeptide immunoreactive with human MAb L92 has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Transformed cells are generally understood to be those cells which have an inserted plasmid vector which is capable of replication within the said transformed cells. Transfected cells are generally understood to be those which have been infected with a viral vector or a virally derived vector. In both cases, the vector may carry a segment of DNA which encodes for the protein or peptide of interest and which is capable of being replicated and expressed along with the DNA of the plasmid or viral vector. It is sometimes possible through manipulation of the growth conditions of the cells to "overproduce" the desired protein or peptide such that it is the major protein expressed in the cell.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

Another embodiment of the present invention is a segment of DNA which encodes the polypeptide sequence designated herein as SEQ ID NO:1, 8 or 9 and its complement, which DNA sequences are depicted in FIG. 4 and designated SEQ ID NOS:6 and 7. It is understood that these DNA sequences may be used as probes to identify complementary stretches of DNA from an organism or from a vector and that the identified DNA segment may be isolated and cloned by techniques well known in the art, and that all such use of the said DNA segments and the products isolated with the use of said DNA segments are encompassed by the present invention. It is also understood that minor changes in the said DNA sequences may occur through genetic code redundancies, for example, and that such genetic sequences, which encode the said peptide sequences are also included as a part of the claimed invention.

Another embodiment of the present invention is a human antibody and more preferably a monoclonal antibody immunoreactive with the polypeptide sequences designated herein as SEQ ID NOS:1, 8 or 9. The peripheral blood lymphocytes (PBL) of a melanoma patient were used to establish B-cell lines that each produce an antibody to a tumor associated antigen with Epstein-Barr Virus (EBV) transformation techniques (Irie et al., 1982). One of these cell lines produces human monoclonal antibody L92. The said antibody, (HuMAb) L92, was shown to react to a 43 kD protein associated with human tumor cells. This 431 kD protein appears to be a new and unique tumor associated antigen in that it is distinguished from most of the known melanoma associated antigens discussed above by virtue of its relative molecular weight ($M_r$) of 43 kDa, and the available sequence data.

For example, the 10 amino acid sequence reactive to HuMAb L92 did not match the sequence of any reported protein including cytokeratin 18. This distinguishes HuMAb L92 from the human monoclonal antibodies 16.88 and C-OU 1. These later two antibodies react with another 43 kD protein molecule in human cancer cells whose amino acid sequence is partially known and which exhibits about 70% identity with cytokeratin 18. Because HuMAb L92 exhibits no identity with the cytokeratin 18, it is believed that these two antibodies recognize different molecules or epitopes than does HuMAb L92.

The similarity of HuMAb 192 to MS2B6 is not known, but the immunoreactive band with HuMAb L92 on Western blotting has produced a sharp and clear band of 43 kD, indicating that HuMAb L92 detects a different antigenic epitope than does MS2B6. Since the amino acid sequences of these 43 kDa or near 43 kDa proteins are not known, exact comparison is not possible. The possibility these antigens detect different epitopes on the same molecule has not been excluded. This will be clarified when a fill length amino acid sequence of the protein(s) is determined.

To identify the gene encoding the antigenic epitope, a cDNA expression library constructed from the human melanoma cell line UCLASO M14 (Irie et al., 1976) was screened with HuMAb L92. DNA sequence analysis of the isolated clone revealed that the antigenic epitope was a 10 amino acid peptide. Further testing revealed that a four amino acid peptide (Lys-Tyr-Gln, SEQ ID NO:8) contained within the 10 amino acid peptide is the minimum antigenic epitope of HuMAb L92. The peptide was expressed in *E. coli* as a β-galactosidase-peptide fusion, and as a glutathione-S-transferase (GST)-protein fusion.

A cDNA expression library is a group of vectors containing cloned DNA segments, cloned generally from poly A⁺ mRNA, such that only actively transcribed message is cloned into the library. Thus, the DNA segments inserted in the library vectors are complementary only to RNAs that are actively transcribed or expressed in the particular cell line from which the library is derived.

The human monoclonal antibody referred to herein as HuMAb L92 is another embodiment of the present invention. The antibody is expressed by a B-cell line developed by the inventor and is immunoreactive with the 43 kDa melanoma associated antigen and peptides designated herein as SEQ ID NOS:1, 2 and 8. It is understood that this antibody is useful for screening samples from human patients for the purpose of detecting melanoma associated antigens present in said samples. The said antibody may also be useful in the screening of expressed DNA segments or peptides and proteins for the discovery of related antigenic sequences. All such uses of the said antibody and any antigens or epitopic sequences so discovered fall within the scope of the present invention.

Another embodiment of the present invention is an antigen composition comprising a protein or polypeptide which is immunoreactive with HuMAb L92 in an amount effective to elicit a CTL or antibody response. Preferably the polypeptide composition will include the polypeptide sequences designated herein as SEQ ID NOS:1, 8 or 9, singly or in combination and may also include the sequence of a carrier protein such as β-galactosidase. It is contemplated that the polypeptide will be present in the composition at a concentration of between 1 mg/ml and about 10 mg/ml and preferably at about 5 mg/ml. The polypeptide composition discussed in the present paragraph may also be a component of a polyvalent melanoma cell vaccine (MCV).

A polyvalent melanoma cell vaccine is for example, a vaccine which comprises several melanoma cell lines which express multiple melanoma associated antigens. The cells are rendered inviable, preferably by irradiation, and administered to a patient in order to elicit an immune response as discussed elsewhere (Morton et al., 1992, incorporated herein by reference).

As is shown herein, the melanoma cells of the MCV may be rendered more effective by pre-immunization with the peptide segment designated SEQ ID NO:1. Therefore, the cells may or may not be pretreated, and the polypeptide composition which includes the polypeptide sequences of the present invention may be administered in conjunction with the MCV. It is contemplated that a method of treating human cancer patients and preferably, human melanoma patients would comprise administering to said patients a polyvalent melanoma cell vaccine about every two weeks for three times and then about once a month for about a year, followed by administration about every 3 months for about four times and then about every six months thereafter, and further comprising administering a composition comprising the polypeptide sequence herein designated as SEQ ID NO:1 or no:8 or no:9 about every four weeks for two to four times and then about every six months thereafter.

Alternatively, the present invention may be a method of enhancing the immune response in a subject comprising the steps of obtaining cytotoxic lymphocytes from said subject, contacting said cytotoxic lymphocytes with a polypeptide according to SEQ ID NO:1, SEQ ID NO:8 or SEQ ID NO:9 and reintroducing said lymphocytes into said subject. The enhanced immune response may be an active or a passive immune response. Alternatively, the response may be part of an adoptive immunotherapy approach in which the lymphocytes are pulsed with the polypeptide and then reintroduced into the subject. In certain embodiments, the subject is a human cancer patient and more preferably a human melanoma patient. The lymphocytes may be obtained from the serum of the subject, or alternatively from tumor tissue to obtain tumor infiltrating lymphocytes as disclosed in Rosenberg et al., *Science,* vol 233, page 1318, incorporated herein by reference. In certain preferred embodiments, the lymphocytes are peripheral blood lymphocytes and in other embodiments, the method of enhancing the immune response is practiced in conjunction with melanoma whole cell therapy.

It is understood that although clinical applications for the polypeptide and nucleic acid sequences, antibodies and recombinant cell lines of the present invention are disclosed, that the various embodiments of the invention will have other important utilities, such as the screening of tissue and culture samples for the presence of melanoma associated antigens and in the development of new therapeutic and prophylactic agents for use against melanoma. Further, the polypeptides and antibodies of the present invention are useful for advancing the general knowledge and use of antigenic sequences, antibodies and activated cellular immune systems in the search for immunogenic weapons against various diseases.

FIG. 1A, Western blot of M14 cells with HuMAb L92.

FIG. 1B, Western blot of M14 cells with non-specific human IgM.

FIG. 1C, SDS-PAGE analysis of proteins stained with Coomasie Brilliant Blue.

In FIGS. 1A–C: Lane 1, molecular weight standard; Lane 2, M14 Human melanoma cell line grown in human AB serum; Lane 3, M14 human melanoma cell line grown in media containing fetal calf serum; Lane 4, M12 human melanoma cell fine grown in media containing fetal calf serum; Lane 5, fetal brain, second trimester.

FIG. 2. Reactivity of HuMAb I92 to ³⁵S-methionine-labeled M14 human melanoma cell line. Biotin-labeled anti-human IgM antibody was used as a second antibody. Lane 1, whole cell extract; Lane 2, immunoprecipitate without HuMAb L92; Lane 3, immunoprecipitate with HuMAb L92; Lane 4, immunoprecipitate with HuMAb L612.

Figures 3A, 3B:
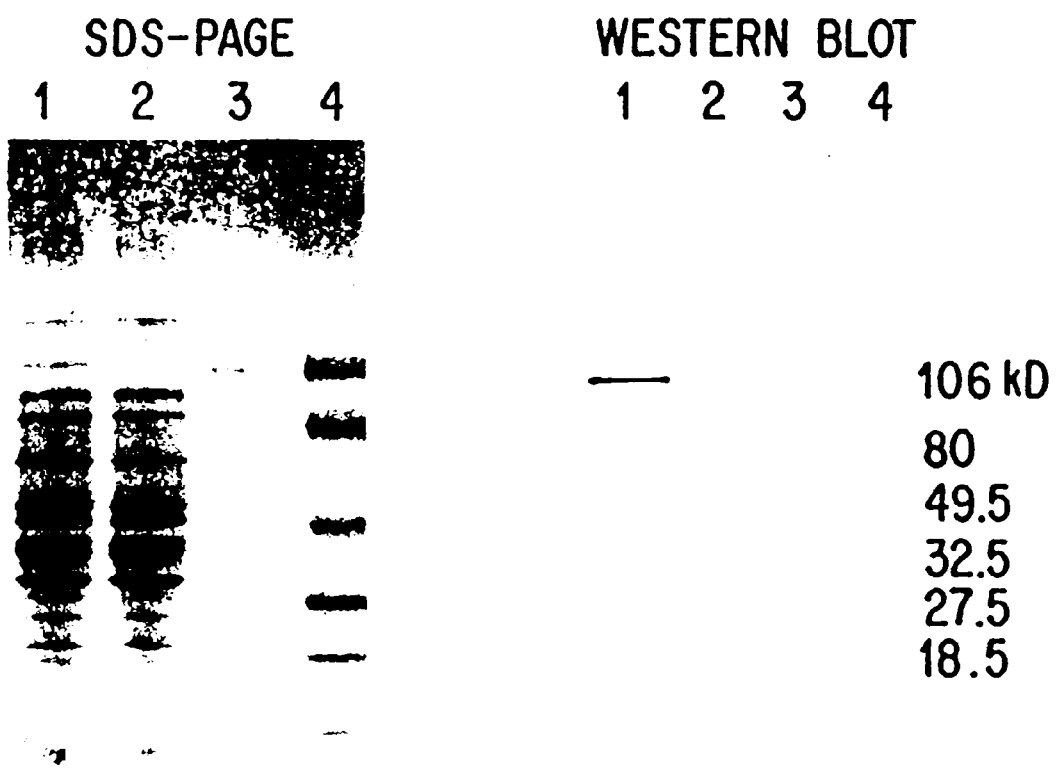

FIG. 3A. Expression of immunopositive fused protein in *E. coli* analyzed by SDS-PAGE of the protein stained with Coomasie Brilliant Blue.

FIG. 3B. Expression of immunopositive fused protein in *E. coli* analyzed by Western blot using HuMAb L92.

In FIGS. 3A–B: Lane 1, *E. coli* lysogen containing immunopositive #810 clone-protein, SEQ ID NO:2; Lane 2, same as Lane 1 without IPTG induction; Lane 3, β-galactosidase; Lane 4, molecular weight standard.

FIG. 4. The double stranded nucleotide sequence and deduced amino acid sequence of immunopositive clone

810. The amino acid sequence is the sequence designated SEQ ID NO:2. The upper DNA sequence is designated SEQ ID NO:6 and lower, complementary sequence is designated SEQ ID NO:7.

Figures 5A, 5B:
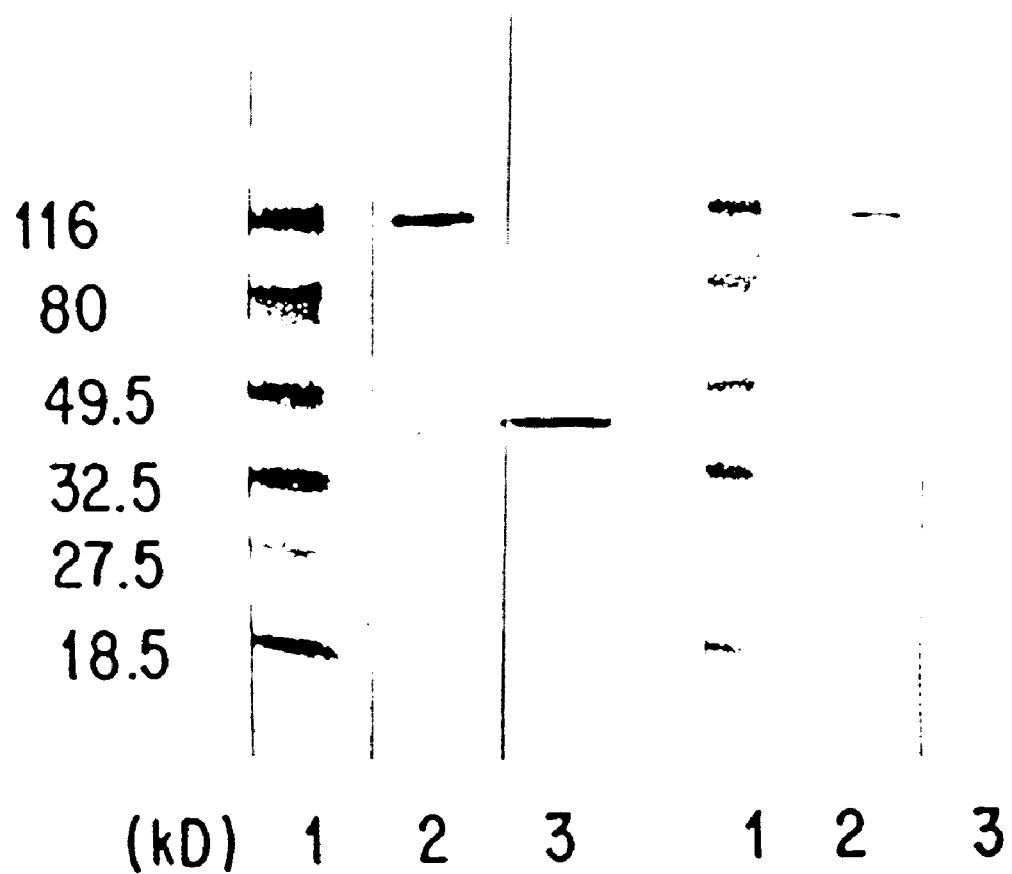

FIG. 5A. Competition of synthetic peptide (DSRPQDLTMKYQIF, SEQ ID NO:2) for the binding of HuMAb L92 to the protein of the melanoma cell line analyzed by immunostaining HuMAb L92 pre-absorbed with the synthetic peptide, SEQ ID NO:2.

FIG. 5B. Competition of synthetic peptide (DSRPQDLTMKYQIF, SEQ ID NO:2) for the binding of HuMAb L92 to the protein of the melanoma cell line analyzed by immunostaining with HuMAb L92 post-absorbed with the synthetic peptide, SEQ ID NO:2.

FIGS. 5A–B: Lane 1, molecular weight standard; Lane 2, lysogen from clone #810; and Lane 3, M14 melanoma lysates.

Figure 6:
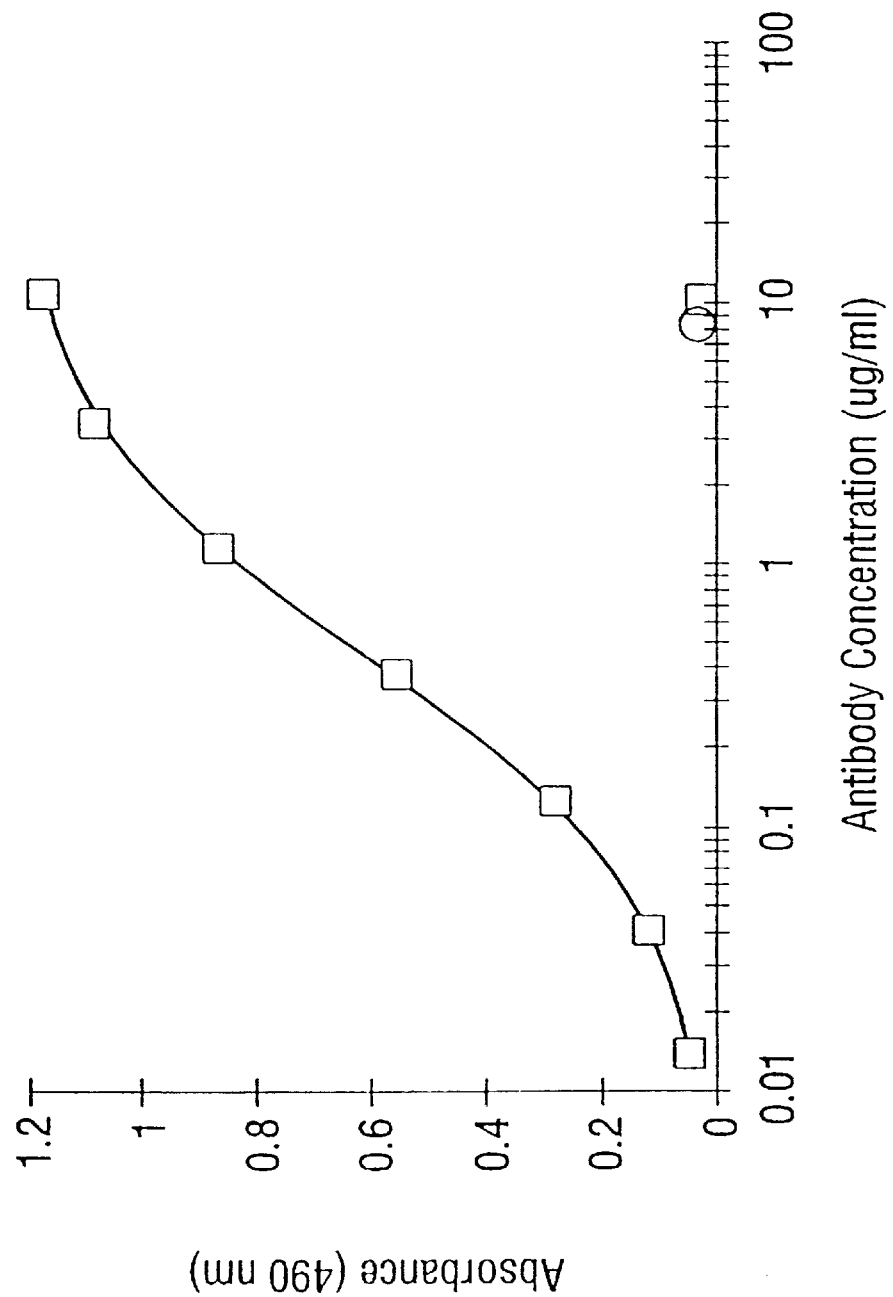

FIG. 6. Reactivity of HuMAb L92 to synthetic peptide (QDLTMKYQIF, SEQ ID NO:1) in ELISA. A 10 amino acid peptide was immobilized on ELISA plates (Reacti-Bind™, PIERCE), according to the manufacturer's instructions. ■=HuMAb L92; ○=10 µg/ml of unrelated human IgM (L612); and □=without HuMAb L92.

Figures 7A, 7B:
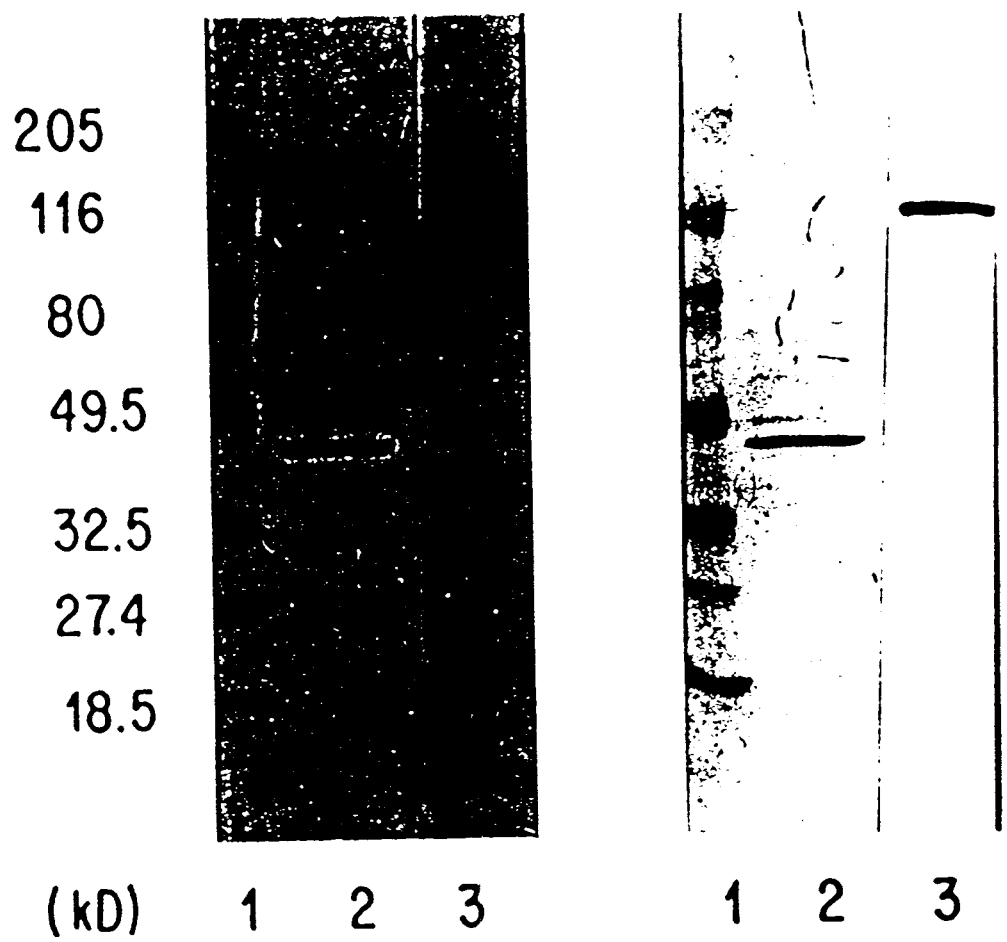

FIG. 7A. Detection of the 43 kD protein on the surface of the M14 cell by Western blot analysis. The L92 HuMAb antibody was incubated with M14 cells ($\geq 3\times 10^{10}$ cells) overnight at 4° C. After centrifugation, the supernatant antibody was tested for its reactivity to the 43 kD protein and #810, SEQ ID NO:2 fused protein.

FIG. 7B. Control reaction of detection of the 43 kD protein on the surface of the M14 cell by Western blot analysis in which L92 HuMAb was incubated overnight without M14 cells.

In FIGS. 7A–B: Lane 1, molecular weight standard; Lane 2, M14 cell lysates; Lane 3, #810 antigen, SEQ ID NO:2.

FIG. 8A. Diffuse cytoplasmic signals are visible in melanoma M14 cells (Magnification ×200). The cells are hybridized against the #810 antisense probe.

FIG. 8B. The melanoma M14 cells are hybridized against the #810 sense probe.

Figure 9A:
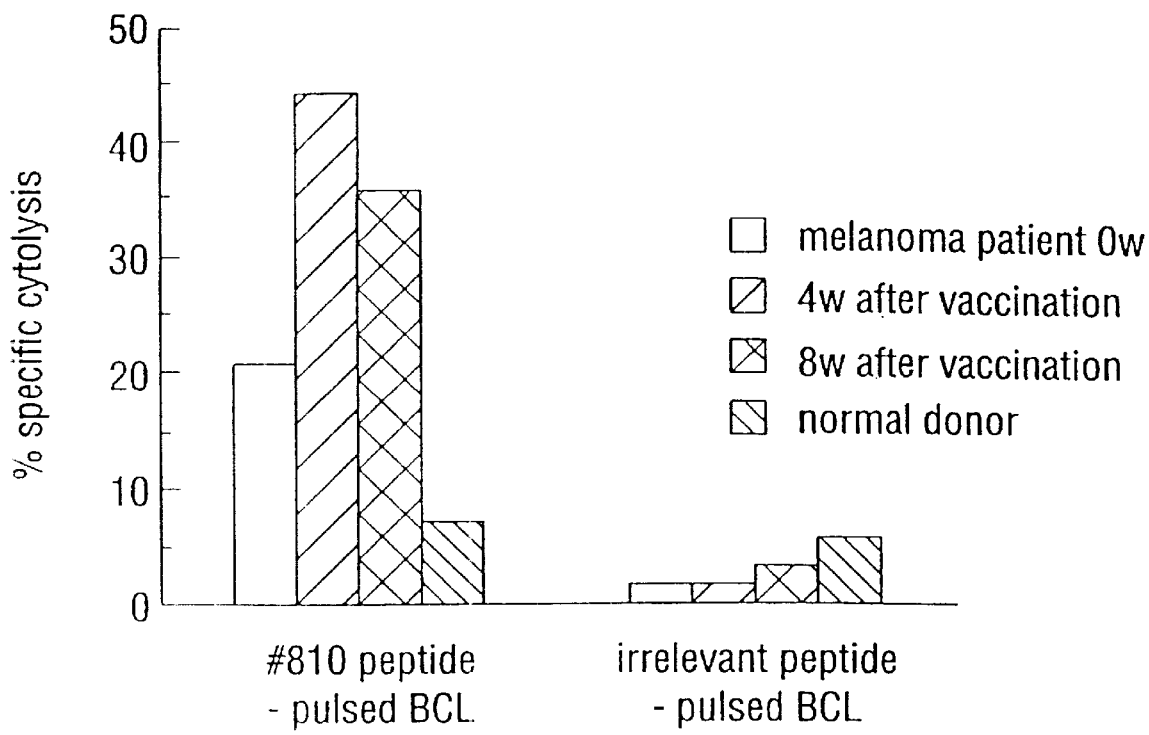

FIG. 9A. Cytotoxicity against autologous BCL pulsed with #810 peptide, SEQ ID NO:1. Cytotoxicity and proliferation assays were performed as described herein. Representative data of 19 patients and 19 control normal donors are shown. At 0, 4 and 8w, a patient's PBMC show positive cytolyses ($\geq 17\%$ at E:T of 80:1) of autologous #810-pulsed BCL while those of a normal donor do not. Lysis of autologous BCL without peptides did not exceed 7% by any effector. Mean cpm±SD of triplicate cultures are shown in (B). At 4 and 8w, values of the patient's PBMC with #810 peptide, SEQ ID NO:1, 0.001–20 µM are significantly higher than those without #810, SEQ ID NO:1 ($p<0.005$) and maximal SIs were 2.71 and 2.87 at 4 and 8w, respectively whereas significant proliferative response to #810, SEQ ID NO:1, is not observed before vaccination (0w) and in a control donor.

Figure 9B:
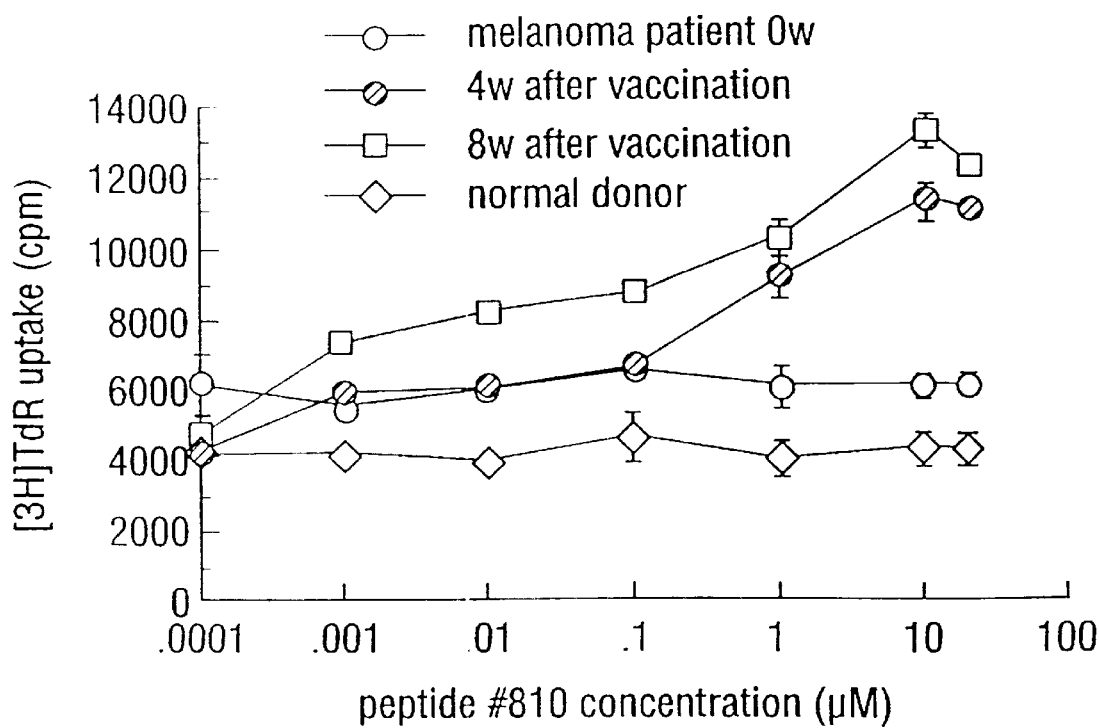

FIG. 9B. Proliferative response to #810, SEQ ID NO:1 of PBMC from a vaccinated melanoma patient. Assays were done as described in 9A.

Figure 10:
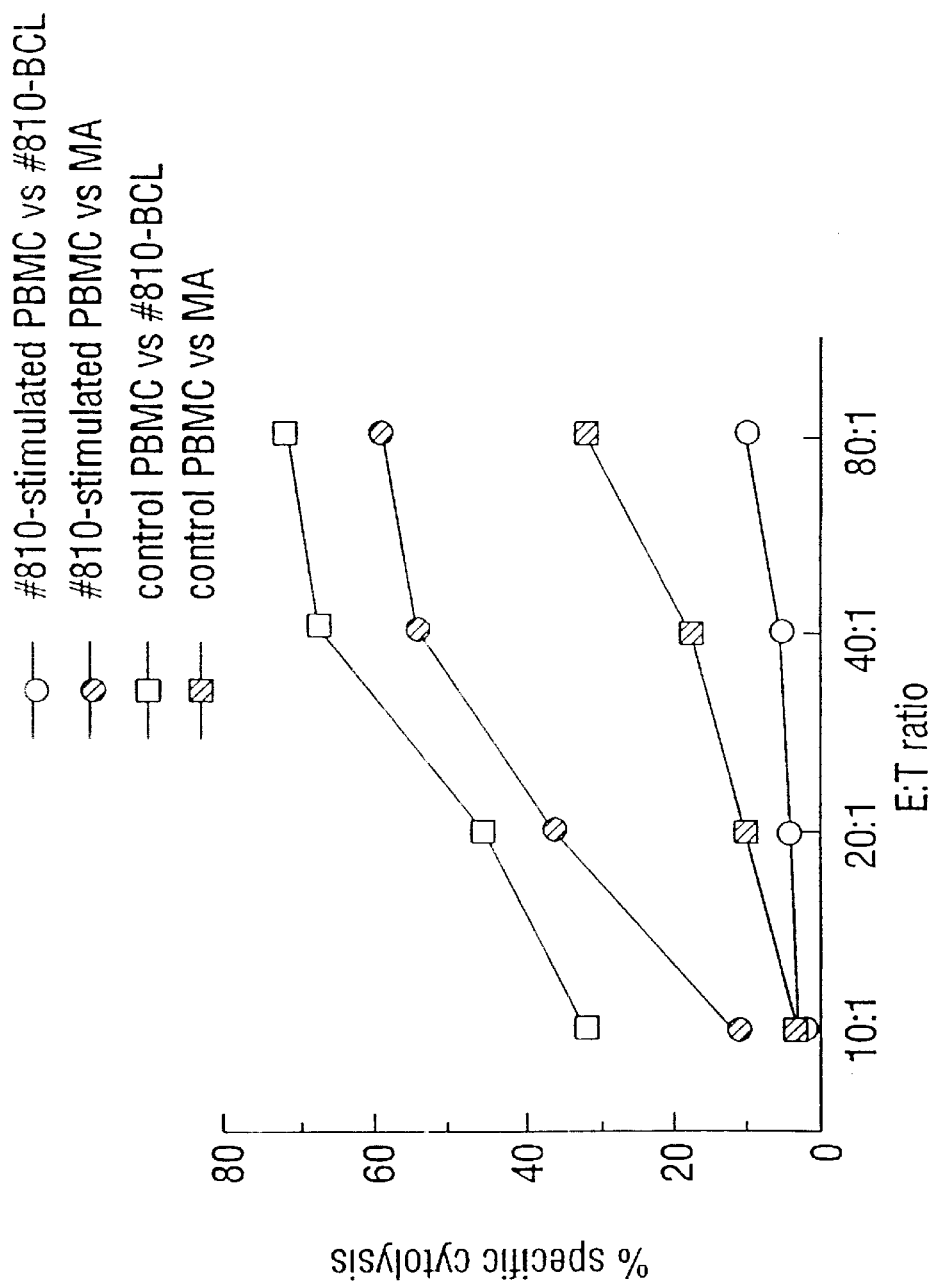

FIG. 10. Cytotoxicity of a patient's PBMC restimulated with #810, SEQ ID NO:1 in vitro. PBMC from patient A 4w after vaccination were in vitro restimulated with #810 and were assayed for cytolyses of autologous #810, SEQ ID NO:1—pulsed BCL and melanoma MA targets as described herein. □ and ○ indicate cytotoxicity of control PBMC cultured with medium only. Lysis of autologous BCL without peptides or pulsed with an irrelevant decapeptide did not exceed 8% at an E:T of 80:1 by an either effector. Lysis of K562 by #810, seq id n1:1—restimulated PBMC and control at E:T of 80:1 were 24.0 and 24.5%, respectively. Data are representative of three separate studies.

Figure 11A:
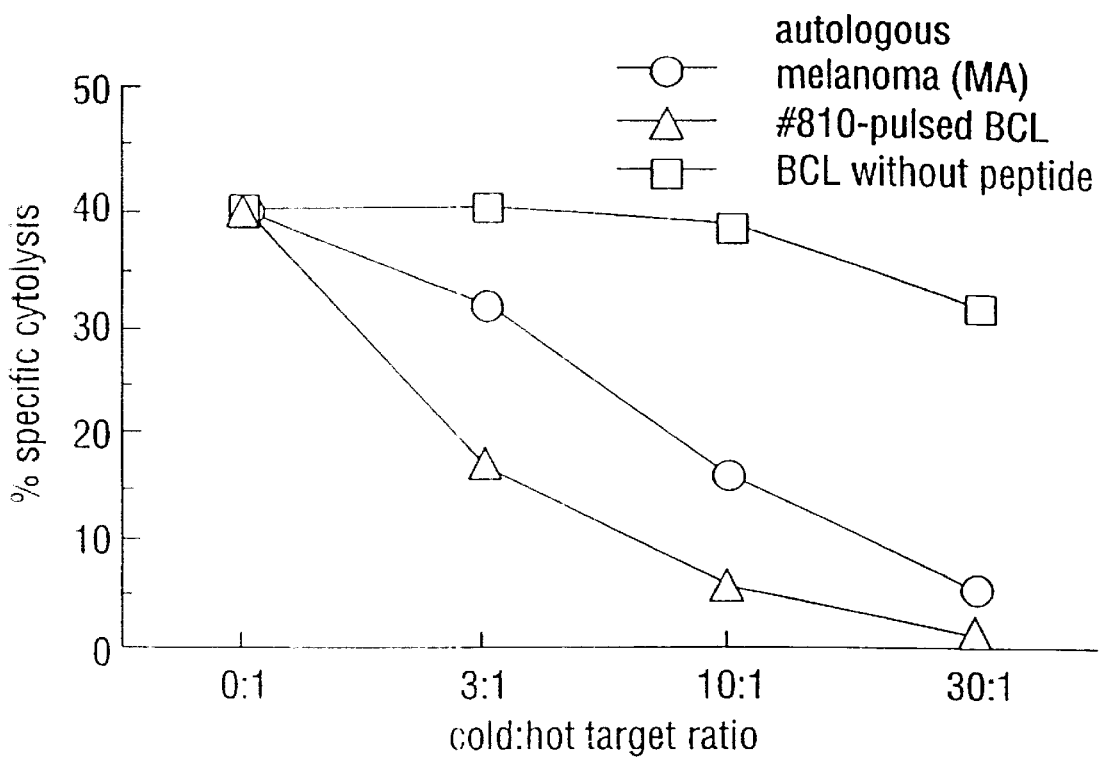

FIG. 11A. Cytolysis of autologous #810, SEQ ID NO:1—pulsed BCL. Cold target inhibition of cytolyses of autologous #810, SEQ ID NO:1—pulsed BCL and melanoma MA. PBMC from patient A were restimulated with #810, SEQ ID NO:1 similarly to FIG. 10 and assayed for cytolyses of autologous $^{51}$Cr-labeled #810, SEQ ID NO:1—pulsed BCL (A) and melanoma MA (B) at E:T of 20:1. Unlabeled cold target cells were added at indicated ratios. Lysis of BL without peptides was 3.0% at E:T of 20:1. Data are representative of four separate experiments.

Figure 11B:
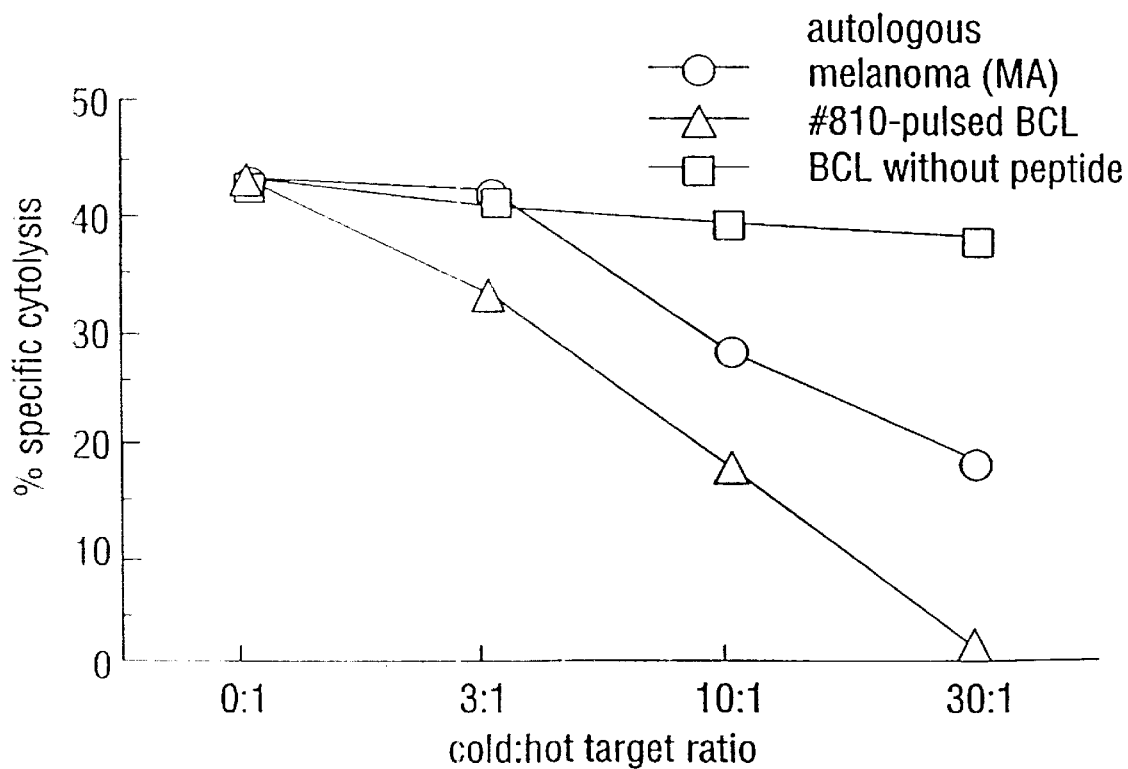

FIG. 11B. Cytolysis of melanoma MA as described in FIG. 11A.

Figure 12:
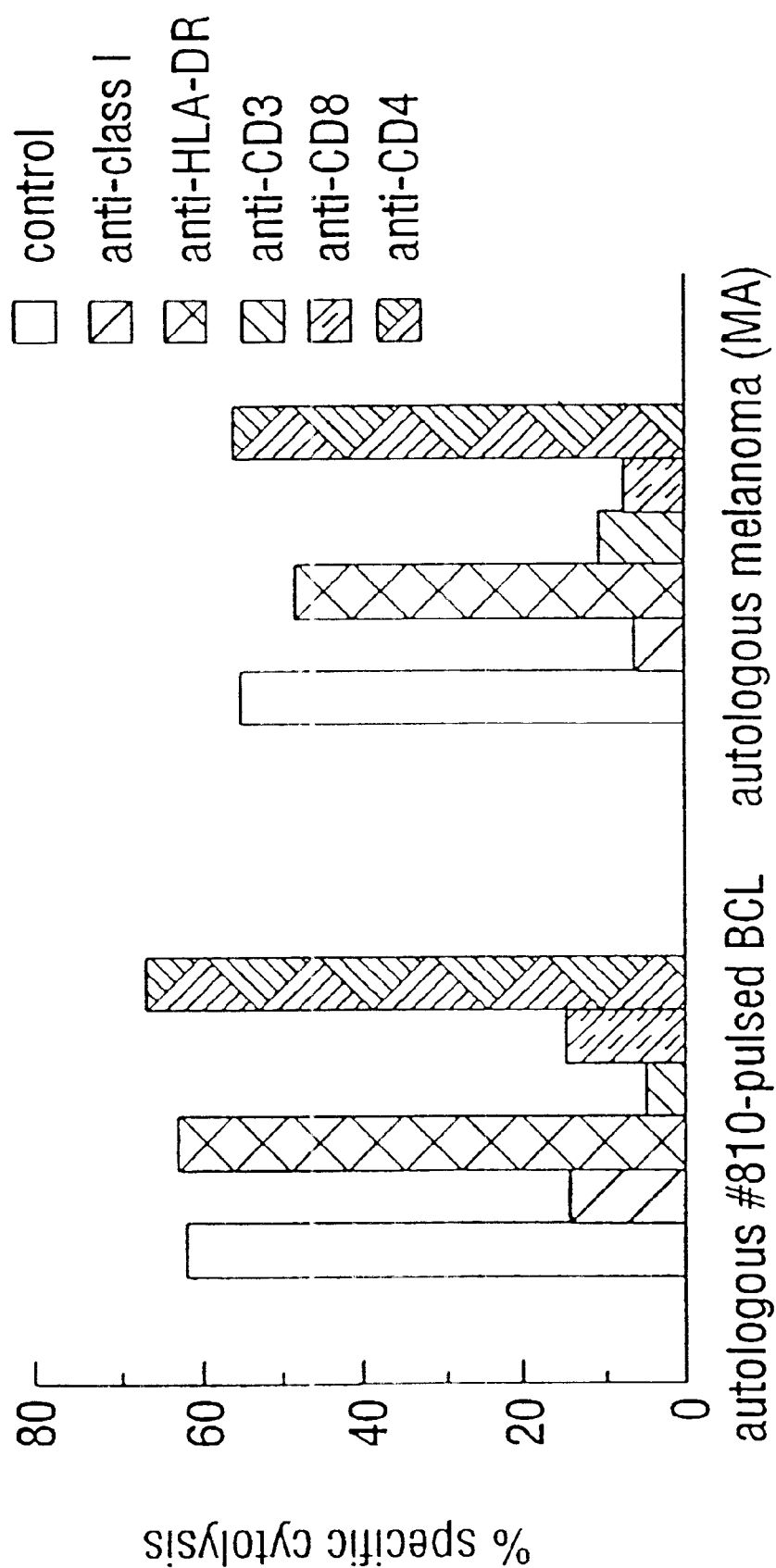

FIG. 12. Antibody inhibition of cytotoxicity by #810, SEQ ID NO:1—restimulated PBMC. #810, SEQ ID NO:1—restimulated PBMC from patient A were assayed for cytolyses of autologous #810, SEQ ID NO:1—pulsed BCL and melanoma MA at E:T of 40:1 in the presence or absence of antibodies. A final concentration of each antibody was 10 µg/ml. Lyses of autologous BCL without peptides and pulsed with an irrelevant decapeptide were 5.4 and 5.2%, respectively. Data are representative of four separate experiments.

Figure 13A:
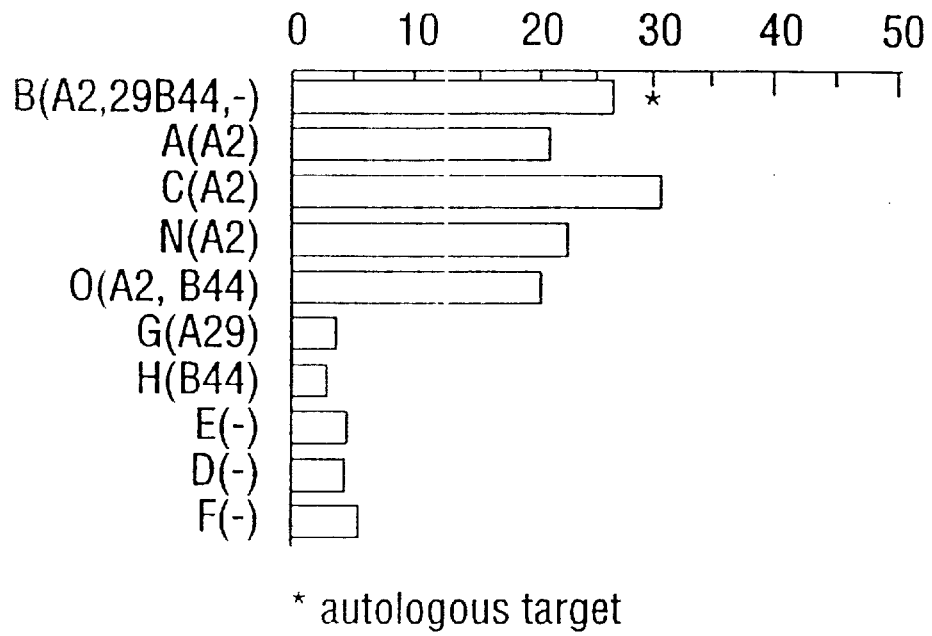
Figure 13B:
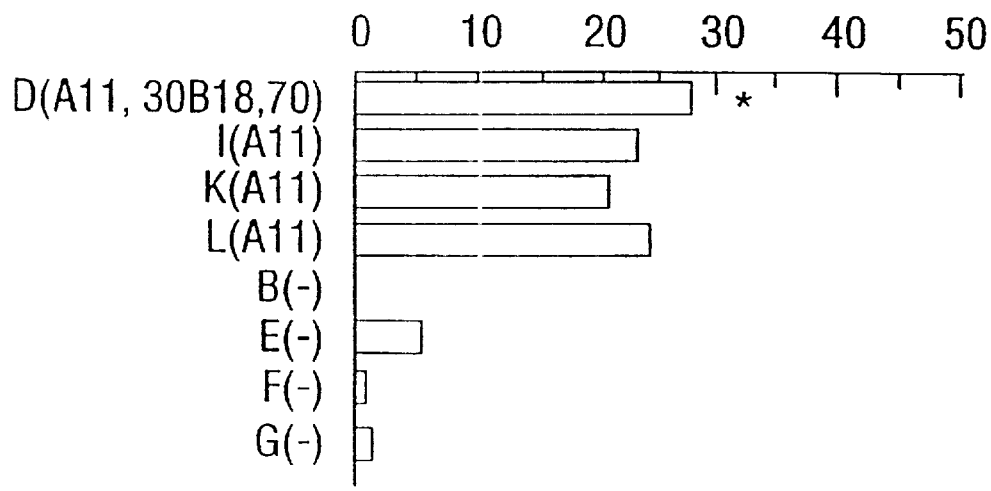

FIG. 13. Cytolyses of autologous and allogeneic #810, SEQ ID NO:1—pulsed BCL by #810, SEQ ID NO:1—restimulated PBMC. Representative data of three experiments are shown as % specific cytolysis at E:T of 40:1 against #810, SEQ ID NO:1—pulsed BCL targets. Effectors are #810, SEQ ID NO: 1—restimulated PBMC of patient B (HLA-A2+) and D (HLA-A11+). Parentheses of left margin indicate HLA-A or B antigens shared between the effectors and targets. Each autologous and allogeneic target was also preincubated in media only or pulsed with an irrelevant decapeptide, and was tested for lysis by the effectors. Lysis of those control targets did not exceed 5% by an either effector.

Figure 14:
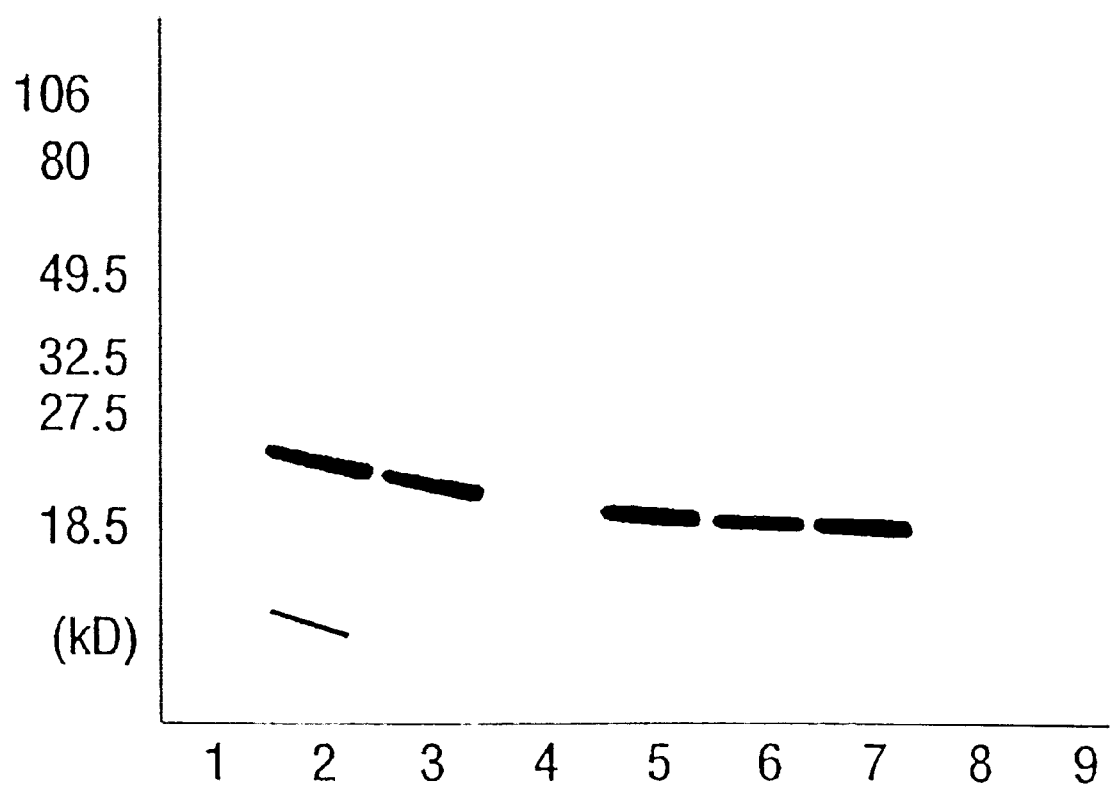

FIG. 14. Determination of minimal antibody recognition peptide.

Several GST-fused peptides were truncated from the 10 amino acid HuMAb L92 immunoreactive peptide sequence (SEQ ID NO:1) were prepared using synthetic oligonucleotides and pGEX-2T as the vector. While the truncation of 1 amino acid residue from the C-terminus did not affect the binding of HuMAb L92 (Lane 3), the removal of 2 C-terminal amino acid residues completely deleted antibody binding (Lane 4). The deletion of 6 amino acid residues from the N-terminus of the 10 amino acid peptide did not affect the binding of HuMAb L92 (Lane 7), but the removal of 7 N-terminal amino acids again deleted antibody binding (Lane 8).

The inventors have previously developed a number of B-cell lines that produce human monoclonal antibodies reactive to melanoma cell lines (Irie et al., 1982) using Epstein-Barr virus (EBV) transformation techniques. One particular B-cell line produced HuMAb L92 from a melanoma patient's peripheral blood lymphocytes (PBL). HuMAb L92 is an IgM-class antibody that reacts to several types of human cancer cells but does not respond to normal cells by the immunoadherent assay which specifically detects surface antigens (See Table 1). The ability of antigen (s) to bind with HuMAb L92 was not altered by treatment with glycosidases such as βgalactosidase, α-mannose, neuraminidase, and α-fucosidase. HuMAb L92 was devoid of reactivity to gangliosides and neutral glycolipids purified from antigen-positive melanoma cells. This indicated that L92 recognized a protein or peptide antigen.

HuMAb L92 was used to identify and clone a gene encoding the immunoreactive epitope of a 43 kD protein associated with human cancer cells. The epitope-encoding gene encodes a newly discovered 10 amino-acid sequence (SEQ ID NO:1), as well as a 4 amino acid sequence (SEQ ID NO:8) contained within the 10 amino acid segment which has been expressed in the form of a protein-peptide fusion with β-galactosidase and GST in *E. coli*. HuMAb L92 specifically bound to both the protein-peptide fusion and the synthetic peptide alone. Absorption of HuMAb L92 with melanoma cells has proven that the antigen is predominantly expressed inside the cell of certain melanomas, while a high density of the antigen is expressed on the cell surface of other melanomas.

The nucleotide sequence encoding the peptide was determined by dideoxy sequencing, a technique well known to those of skill in the art. This sequence was screened for homology to all known sequences contained in the Genebank database and no homology was found between the cloned sequence and any other reported DNA sequence.

M14 lysates were prepared after the cells were pulsed with $^{35}$S-methionine for 4 hrs. After the cell lysate was precleaned with anti-human IgM-biotin and Streptavidine agarose, HuMAb L92 was added and incubated. Either the unrelated HuMAb L612 (Yamamoto S et al., 1990), or buffer alone, was added to the precleaned cell lysate. The immune complex was then precipitated with anti-human IgM-biotin and Streptavidine agarose, and the precipitates were subjected to SDS-PAGE followed by autoradiography. Immunoprecipitates with HuMAb L92 showed a clear band at 43 kD. However, the immunoprecipitate, either with HuMAb L612 or without primary antibody, failed to show the band (FIG. 2), indicating that the 43 kD protein band in Lane 3 specifically binds to HuMAb L92.

Western blot analysis showed that the protein-peptide fusion bound specifically to HuMAb L92. An antigen-encoding peptide of 10 amino acids was synthesized and tested for its immunoreactivity in vitro. HuMAb L92 reacted specifically to the 10 amino acid peptide in both an antibody inhibition assay and a solid-phase ELISA. The HuMAb L92 also was shown by Western blot analysis to react with the four amino acid peptide designated as SEQ ID NO:8. These results suggest that the identified peptide sequences comprise immunogenic epitopes of the 43 kD protein that induces immune responses in man.

Abbreviations

The following abbreviations are used throughout the present disclosure. HuMAb, human monoclonal antibody; ELISA, enzyme-linked immunosorbent assay; PBL, peripheral blood lymphocytes; FCS, fetal calf serum; PCR, polymerase chain reaction; IPTG, isopropyl thiogalactosidase; SDS-PAGE, sodium dodecyl sulfate-polyacrylamide gel electrophoresis; TAA, tumor-associated-antigens; CTL, cytotoxic T lymphocyte; MCV, melanoma cell vaccine; MAA, melanoma-associated antigen; BCL, Epstein-Barr virus-transformed B lymphoblastoid cell line; IA, immunoadherence; PBMC, peripheral blood mononuclear cells; [$^{3}$H]TdR, tritiated thymidine; SI, stimulation index; LAK, lymphokine-activated killer.

Synthetic Peptides

Peptide #810 (QDLTMKYQIF, SEQ ID NO:1) and an non-immunogenic decapeptide of irrelevant sequence (IMTQLFQDYK, SEQ ID NO:5) were synthesized in the Beckman Research Institute of the City of Hope (Duarte, Calif.) using the 9'-fluorenylmethoxycarbonyl (FMOC) method. Those peptides were purified by high-pressure liquid chromatography. The peptides were more than 95% pure. The identity of the peptides was confirmed by a high resolution mass spectrum.

Tumor Cell Lines

Melanoma cell lines, gastric, colon, lung and breast cancer cell lines, erythroleukemia K562 and Epstein-Barr virus transformed B lymphoblastoid cell lines (BCL) were all cultured by RPMI 1640 medium (JRH Biosciences, Lenexa, Kans.) supplemented with 10% heat-inactivated fetal bovine serum (Gemeni Bioproducts, Calabasas, Calif.).

Western Blotting

Cell lysate was analyzed for the presence of 43 kD protein using L92 antibody by Western blotting. Briefly, cells were harvested, pelleted and dissolved in lysis buffer (50 mM Tris-HCl, 5% β-mercaptoethanol, 2% sodium dodecyl sulfate, 0.1% bromophenol blue, 10% glycerol). Proteins of cell lysates were separated by polyacrylamide gel electrophoresis in reducing condition. Proteins in a gel were transferred to a nitrocellulose filter. Filters were incubated in phosphate buffered saline containing 5% bovine serum albumin, washed and incubated with primary antibody L92, washed and then incubated with peroxidase-conjugated goat anti-human IgM secondary antibody (Boehringer Mannheim), washed and then coloring reaction was performed by 4-chloro-1-naphtol in methanol with $H_2O_2$.

Immunoadherence (IA) Assays

IA assays were preformed as described herein. Briefly, target cells were incubated with antibody L92 for 90 min at 37° C., washed and then incubated with a guinea pig complement (Whittaker M. A. Bioproducts, Inc., Walkersville, Md.) for 10 min. After complete setting of target cells and erythrocytes for 20 min, erythrocyte rosetting around target cells were examined.

Allogeneic Whole Melanoma Cell Vaccines (MCV)

Melanoma patients may be immunized with MCV as previously reported (Morton et al., 1992). MCV consists of for example, three melanoma cell lines (M10, M24 and M101) which are irradiated and cryopreserved before use. The MCV is thawed, washed and mixed with BCG and then injected intradermally every 2 weeks ×3, then monthly for 1 year, and then every 3 months ×4, finally every six months.

Peripheral Blood Mononuclear Cells (PBMC) from Melanoma Patients and Normal Donors In order to obtain PBMC, patients were bled before (Ow) and at monthly intervals (4, 8 weeks) after the initiation of vaccination. PBMC were separated by Ficoll-Hypaque gradient centrifugation and cryopreserved before testing. PBMC from normal donors were obtained from American Red Cross (Los Angeles, Calif.). BCL were prepared by transformation of those PBMC with Epstein-Barr virus.

Culture Medium

RPMI 1640 supplemented with 10% heat-inactivated human AB serum (Irvine Scientific, Santa Ana, Calif.) was used as culture medium in the following examples.

Monoclonal Antibodies

Human IgM monoclonal antibodies L92 and L612 (anti-ganglioside $GM_3$) were cloned and purified in the inventor's laboratory. Murine IgG monoclonal antibodies anti-HLA class I, anti-HLA-DR, anti-CD3, anti-CD4 and anti-CD8 were purchased from AMAC, Inc., Wesbrook, Me. $^l$Cr labeled targets were preincubated with anti-class I, anti-HLA-DR, L92 or L612 for 1 h at 37° C. before the addition of effector cells. Effector cells were preincubated with anti-CD3, CD4 or CD8 for 1 h before the addition of targets. Those antibodies were used at the final concentration of 10 μg/ml in 6h-cytotoxicity assays. The results were evaluated for statistical significance by the Student's t test.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Immunochemical Analysis

Two methods of immunochemical analysis were preformed in order to identify antigen molecules which were reactive with the HuMAb L92. These included separation of protein solutions by SDS-polyacrylamide electrophoresis followed by Western Blot analysis, in which the proteins are transferred to a nitrocellulose filter and reacted to an antibody which is conjugated to another antibody capable of a calorimetric reaction. The antigens were also subjected to ELISA reactions in which the peptide was placed in microtiter plate wells and reacted with the antibody which was then reacted with the secondary, indicator antibody.

SDS-Polyacrylamide/Western Blot Analysis

Human melanoma cell lines M14 and M12, and human fetal brain cells were tested for their reactivity to HuMAb L92 in Western blotting. Two different media supplements, FCS and human AB serum, were used in the case of the M14 melanoma cell line. To prepare the lysates, cells were lysed in a lysis solution containing NP-40, SDS and deoxycholate.

SDS-polyacrylamide gel electrophoresis followed by Western blot analysis was carried out to detect antigen molecules reactive to HuMAb L92. Sample protein solutions in 50 mM Tris-HCl (pH 6.8; 5% β-mercaptoethanol, 2% SDS, 0.1% BPB, 10% glycerol) were boiled for 5 min. Protein separation was performed in a 4–20% polyacrylamide gradient gel. Proteins were transferred to a nitrocellulose filter and sequentially reacted with HuMAb L92 and peroxidase conjugated goat anti-human IgM antibody (Boehringer Mannheim, Ind.). Colorimetric reactions were performed with 4-chloro-1-napthol as the substrate.

In the resulting blot, a discrete band is seen in each of the cell lysates (FIG. 1A). In a control experiment, an unrelated, purified human IgM was tested against the same cell lysates (FIG. 1B). No corresponding band was detected on the control gel. The molecular weight of the reactive protein was estimated as 43 kD based on its mobility in the SDS-PAGE. Cell lysates obtained from M14 melanoma cells grown in human serum media exhibited the same band, indicating that the protein was not derived from FCS in the culture media.

ELISA Analysis

Peptide ELISA was performed in Reacti-Bind™ Plates (PIERCE), as described in the manufacturer's instructions. Briefly, synthetic peptide was dissolved in 0.1M Sodium phosphate, 0.15M NaCl pH 7.2 and added to ELISA plates (100 μl/well) by overnight incubation at 4° C. ELISA was then performed with HuMAb L92 or L612 using peroxidase conjugated goat anti-human IgM antibody. The color was developed with o-phenylenediamine (OPD, Sigma USA) and read on an ELISA reader at 490 nm.

EXAMPLE II

Immunoprecipitation

Indirect immunoprecipitation of proteins labeled in vivo with $^{35}S$ methionine was performed in order to identify protein molecules reactive to HuMAb L92. Briefly, M14 melanoma cells were cultured in RPMI 1640 media supplemented with 10% FCS in T25 culture flasks (Costar) until they reached 70% confluence. The cells were then washed twice with a media preparation consisting of methionine deficient RPMI 1640 media (Sigma R7130) dissolved in 1 L of double distilled water, to which glutamic acid (0.02 g/L), lysine (0.04 g/L), leucine, (0.05 g/L), and 2 g/L of sodium bicarbonate were added. Two ml of this preparation, supplemented further with 10% dialyzed fetal calf serum (Sigma), were added to the flasks, which were subsequently incubated with 1.85 MBq of $^{35}S$-methionine (Amersham) for 4 hrs. After harvesting and washing twice with PBS, the cells were lysed with 100 ul of lysis buffer consisting of 50 mM Tris-HCl (pH 8.0), 150 mM NaCl, 0.02% sodium azide, 0.01% SDS, 100 ug/ml phenylmethyl sulfonyl fluoride (PMSF), 1% NP-40, and 0.5% sodium deoxycholate.

Forty microliters of the cell lysate was diluted to 300 ul with lysis buffer. The diluted lysate was precleaned by incubation with 20 ul of goat anti-human IgM-biotin (Boehringer) for 1 hr on ice and then incubated with 100 ul of Streptavidin-agarose (Sigma) for an additional 1 hr. The supernatant was collected via centrifugation and divided into 3 aliquots. One aliquot was incubated with 10 ug of HuMAb L92. The second aliquot was incubated with HuMAb L612 (unrelated antibody), and the third aliquot was incubated in the absence of antibody for 1 hr on ice. Ten microliters of anti-human IgM-biotin was added to each of the three aliquots and incubated for an additional 1 hr. Ten microliters of Streptavidin-agarose was then added to each aliquot and incubated for another 1 hr. The antigen-anti-IgM-biotin-Streptavidin-agarose complex was pelleted via centrifugation and washed three times with 1 ml of lysis buffer followed by washing with 1 ml of 10 mM Tris-HCl (pH 7.0) and 1% NP-40. Immunoprecipitates were analyzed in 4–20% polyacrylamide gradient SDS gels under reducing conditions. The gels were treated with Amplify™ (Amersham) and processed for autoradiography.

EXAMPLE III

Construction of the Expression Library

To isolate the cDNA clones that encode the HuMAb L92 immunopositive protein, a cDNA expression library from M14 cells was constructed using the λgt11 recombinant phage system. Approximately 6×10$^5$ phage were screened and 2 positive clones were obtained, one of which was chosen for subsequent analysis.

Briefly, the M14 cells were cultured in RPMI-1640 media supplemented with 10% FCS and antibiotic (GIBCO, NY). Total RNA was isolated from 5×10$^8$ M14 cells using guanidine isothiocyanate (Chirgwin, J M et al., 1979). Poly A$^+$ RNA was prepared using the Poly A Tract™ mRNA Isolation System (Promega). cDNA was prepared using the Copy™ Kit (Invitrogen). After ligation of an EcoRI adaptor to both ends, cDNA was inserted into the EcoRI site of λgt11 phage DNA. In vitro packaging was performed using Giga-Pak II Gold (Stratagene). The library was amplified once on solid media before screening.

EXAMPLE IV

Screening of the cDNA Library

*E. coli* Y1090 was cultured at 37° C. in LB broth supplemented with 0.2% maltose and 0.5% MgSO$_4$ until the OD600 reached 0.5. Cells were collected and suspended in half of the original volume in 10 mM MgSO$_4$. Cells were infected by the phage library of Example III and plated on LB agar plates (approximately 20,000 plaques per 150 mm plate). The plates were incubated for 3.5 hrs at 42° C. After placing nitrocellulose filters which had been immersed in 10 mM IPTG on the plates, they were incubated for an additional 4 hrs at 37° C. The filters were subsequently immunostained by HuMAb L92 and peroxidase conjugated goat anti-human IgM antibody. The coloring reaction was carried out with 4chloro-naphtol. The plaques which corresponded to a positive signal on the filters were removed from the agar plates and eluted to prepare the phage stock. The screening procedure was repeated until an homogeneous population of immunopositive recombinant bacteriophage was obtained.

EXAMPLE V

Sequencing the cDNA Insert

To characterize the cloned DNA, an attempt was made to subclone the insert DNA into the EcoRI site of pBluescript II (Stratagene). However, the insert DNA could not be isolated with EcoRI digestion. Therefore, whole phage DNA was used as the template to determine the DNA sequence. A partial nucleotide sequence of the cDNA insert in the recombinant λgt11 phage was determined using the Double Stranded DNA Cycle Sequencing System (BRL, Gaithersburg, Md.).

As shown in FIG. 4, this clone has a one base deletion at the EcoRI site, which made it impossible to subclone the insert into the ECoRI site of the plasmid. Although the insert DNA of this clone is 1.4 kbp, it has only a 10 amino acid open reading frame after the EcoRI linker sequence. A search for homology between the open reading frame sequence of the insert and the reported DNA sequences in GeneBank, however, revealed no significant homology.

EXAMPLE VI

Bacterial Expression of the Protein-Peptide Fusion

To determine the antigenicity of the cloned cDNA, it was expressed as a fused protein with β-galactosidase in the E. coli lysogen system and the recombinant protein was analyzed by a Western blot (FIG. 3). Fifty microliters of recombinant phage lysogen which had been cultured overnight at 32° C. were inoculated in 5 ml of LB/ampicillin liquid media and cultured at 32° C. with shaking. When the OD600 reached 0.5, the temperature was shifted to 42° C. for 10 min. Isopropyl β-D-thioglactoside (IPTG) was added to the culture with a final concentration of 1 mM. Cells were cultured at 37° C. for 2 hrs, harvested via centrifugation, and analyzed by SDS-PAGE.

HuMAb L92 reacted with a band at 106 kD in the Western blot (FIG. 3, Lane 1). The lysate obtained from a control experiment (without IPTG induction) did not show this band (Lane 2). In Lane 3, β-galactosidase shows a clear band in CBB staining, however, this band also does not bind HuMAb L92. These data indicate that the amino acids derived from the cDNA portion of the , β-galactosidase-peptide fusion exhibit antigenicity against HuMAb L92.

EXAMPLE VII

Antibody Recognition of a Cloned Oligopeptide

An oligopeptide was synthesized based on the deduced amino acid sequence of the cDNA and it was tested for its ability to inhibit HuMAb L92 binding to the recombinant protein-peptide fusion and to M14 cell lysates. HuMAb L92 was pre-incubated with 500× molar excess of a 14 amino acid peptide (DSRPQDLTMKYQIF, SEQ ID NO:2). This peptide sequence contains the amino acid sequence derived from the cDNA open reading frame and an additional four amino acids derived from the EcoRI adaptor. HuMAb L92 that was not preincubated with the 14 amino acid peptide formed a discrete band with both the protein-peptide fusion and M14 cell extracts at 106 kD and 43 kD, respectively (FIG. 5A). However, HuMAb L92 that was preincubated with the peptide exhibited a significant reduction in reactivity and formed only a faint band on the Western blot (FIG. 5B).

The 10 amino acid peptide (QDLTMKYQIF, SEQ ID NO:1) which corresponds to the cDNA open reading frame showed similar binding inhibition of HuMAb L92 to the protein-peptide fusion and M14 cell lysates in a Western blot analysis. The direct binding reaction of HuMAb L92 to the 10 amino acid peptide was also examined by an ELISA assay. A strong and specific reaction was demonstrated using 1 μg of peptide per well (FIG. 6). These results indicate that the 10 amino acid oligopeptide has antigenicity to HuMAb L92.

In order to further determine the minimum length required for the antigenic epitope of HuMAb L92, several GST-fused peptides that were truncated from the 10 amino acid immunoreactive peptide sequence (SEQ ID NO:1) were prepared using synthetic oligonucleotides and pGEX-2T as the vector. While the truncation of 1 amino acid residue from the C-terminus did not affect the binding of HuMAb L92 (FIG. 14), the removal of 2 C-terminal amino acid residues completely deleted antibody binding (Lane 4). The deletion of 6 amino acid residues from the N-terminus of the 10 amino acid peptide did not affect the binding of HuMAb L92 (Lane 7), but the removal of 7 N-terminal amino acids again deleted antibody binding (Lane 8). These results demonstrate that the minimum antigenic epitope of HuMAb L92 is a 4 amino acid peptide (Lys-Tyr-Gln-Ile, SEQ ID NO:8).

EXAMPLE VIII

Localization of the 43 kD Protein in Melanoma Cells

To determine whether the 43 kD protein is expressed on the cell surface or remains inside the cell, HuMAb L92 was absorbed with intact M14 cells and then allowed to react to the recombinant protein-peptide fusion and to the 43 kD protein in a Western blot analysis (FIG. 7). The staining intensities of the 43 kD protein of M14 cell lysate and of the 106 kD protein of #810 lysogen were only slightly reduced after absorption of the antibody with intact M14 cells. This result suggests that the 43 kD) protein is not expressed in significant amounts on the M14 cell surface. However, subsequent analysis of other melanoma cell lines has shown that the density of the 43 kD protein on the cell surface varied widely among cell lines. For example, the UCLASO M25 cell line (Ravindranath M H et al., 1989) expressed the highest degree of the 43 kD protein on the cell surface among 20 human melanoma cell lines tested.

In Situ Hybridization

A synthetic oligodeoxynucleotide sequence complementary to the mRNA for #810 peptide, SEQ ID NO:2 was end-labeled with digoxigenin and used to detect mRNA in a panel of cells. In situ hybridization was performed as described (Morisaki et al., 1992). The cells fixed on glass slides were prehybridized for 1 h at 42° C. in a solution containing deionized formamide, 20× standard saline citrate, Denhardt's solution, heat-denatured sheared herring sperm DNA, yeast transfer RNA and dextran sulfate. #810 antisense probe (5'-AAA GAT CTG ATA TTT CAT AGT CAG ATC CTG-3', SEQ ID NO:3, Molecular Biology Institute, UCLA School of Medicine, Los Angeles, Calif.) was taillabeled with digoxigenin-11dUTP (Boehringer Mannheim, Indianapolis, Ind.) using the DNA tailing kit (Boehringer Mannheim). A negative control was carried out by using #810 sense probe which was complementary to the test (antisense) probe in the reaction. A 27-mer oligonucleotide probe specific to human fibroblast β-actin (5'-GAC GAC GAG CGC GGC GAT ATC ATC ATC-3', SEQ ID NO:4, Clontech Laboratories, Inc., Palo Alto, Calif.) was used for a positive control. Digoxigenin-labeled probe was placed on the cells and incubated at 42° C. overnight. Cells containing #810 peptide mRNA were detected using the Genius non-radioactivenucleic acid detection kit at (Boehringer Mannheim). Slides were incubated with 2% normal sheep serum and 0.3% Triton X-100 at room temperature for 30 min. Anti-digoxigenin antibody was applied to the cells for 3 h at room temperature. A solution containing nitroblue tetrazolium, X-phosphate solution and Levamisole was placed on the cells at room temperature until they developed a satisfactory color (2–5 h).

In situ hybridization showed that mRNA for #810 peptide was commonly expressed in melanomas, non-melanoma tumors and also in normal lymphocytes (Table 1). FIG. 8 shows a representative melanoma cell line. Hybridization with #810 antisense probe revealed dense staining at a single cell level whereas the use of a sense probe exhibited no staining, demonstrating the probe specificity. Western blotting revealed that 43 kD protein including the sequence of #810 amino-acid sequence could be detected in the same cells that expressed #810 mRNA and thus the presence of this protein was not specific to melanomas. However, its localization varied among cell types; a high density of 43 kD protein was located on the cell surface of certain cell lines (M12, M25, SHN, etc.) while it was not detected on the surface of other kinds (M14, M24, normal lymphocytes, etc.), which results were also proven by antibody absorption assays using those cells. The relations between the histology of those cells and the intracellular localization of the 43 kD protein have not been clarified yet.

TABLE 1

Expression of peptide antigen #810 (QDLTMLYQIF, SEQ ID NO:1) and 43 kD protein by tumors and normal cells.

| | mRNA for #810 peptide | 43 kD protein | |
|---|---|---|---|
| | in situ hybridization[a] | Western blot[b] | cell surface IA assay[c] |
| melanoma M10 | + | + | + |
| M12 | ++ | + | +++ |
| M14 | + | + | − |
| M15 | + | + | − |
| M24 | + | + | − |
| M25 | ++ | + | ++++ |
| M101 | + | + | + |
| M111 | + | + | − |
| M112 | + | + | − |
| neuroblastoma SHN | + | + | ++++ |
| colon cancer | | | |
| SW48 | + | + | ++ |
| SW480 | + | + | + |
| gastric cancer | | | |
| MKN28 | + | + | − |
| MKN45 | + | + | ++ |
| lung cancer | | | |
| 130 | + | + | + |
| 135 | + | + | − |

TABLE 1-continued

Expression of peptide antigen #810 (QDLTMLYQIF, SEQ ID NO:1) and 43 kD protein by tumors and normal cells.

| | mRNA for #810 peptide | 43 kD protein | |
|---|---|---|---|
| | in situ hybridization[a] | Western blot[b] | cell surface IA assay[c] |
| breast cancer 645 | + | + | − |
| erythroleukemia K562 | + | + | − |
| B cell lymphoma L14 | + | + | − |
| normal cells in peripheral blood | + | + | − |
| monocytes | | | |
| T cells | + | + | − |
| B cells | + | + | − |
| erythrocytes | ND[d] | − | ND |
| phytohemagglutinin-stimulated blood lymphocytes | + | + | − |

[a]Expression of #810 mRNA was analyzed by in situ hybridization.
[b]Presence of 43 kD protein was analyzed by Western blot using L92 antibody.
[c]Cell surface expression of 43 kD protein was analyzed by immunoadherence (IA) assay using L92. −, target cells forming erythrocyte rosettes are <5% of total; ±, 5–10%; +, 10–20%; ++, 20–50%; +++, 50–75% and ++++, >75%.
[d]Not done.

EXAMPLE IX

A Peptide Vaccine

A peptide which comprises as part of its amino acid sequence, a sequence accordance with SEQ ID NO:1 may be clinically very important as an effective vaccine in inducing anti-tumor humoral and cell-mediated immune responses in cancer patients. The inventors' results have shown that the synthetic peptide has the ability not only to stimulate the proliferation of lymphocytes of melanoma patients who received melanoma cell vaccine, but also to induce cytotoxic T cells in vitro against autologous melanoma cells.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as INF, IL2, IL4, IL8 and others.

Means for conjugating a polypeptide to a carrier protein are well known in the art and include glutaraldehyde, m-maleimidobenzoyl-N-hydroxysuccinimide ester, carbodiimyde and bis-biazotized benzidine. It is also understood that the peptide may be conjugated to a protein by genetic engineering techniques that are well known in the art.

As is also well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.) ISCOMS and aluminum hydroxide adjuvant (Superphos, Biosector).

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The peptide may be formulated into the vaccine in a neutral or salt form. Pharmaceutically acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2ethylamino no ethanol, histidine, procaine, and the like.

The vaccine will be administered in a manner compatible with the dosage formulation, and in such amount as will be therapeutically effective and immunogenic. The quantity to be administered depends on the subject to be treated, including, e.g., the capacity of the individual's immune system to respond. Precise amounts of active ingredient required to be administered depend on the judgment of the practitioner. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application in a solid physiologically acceptable base or in a physiologically acceptable dispersion, parenterally, by injection or the like. The dosage of the vaccine will depend on the route of administration and will vary according to the determination of the practitioner for each particular patient.

EXAMPLE X

Diagnostic Immunoassays and Skin Tests

Immunoassays that measure the degree of specific humoral and cellular immune responses in patients during active, specific immunotherapy can be developed in light of the present disclosure. The peptides and protein of this invention can be evaluated for their vivo immunogenicity and therapeutic efficacy in immunotherapy. A variety of humoral and cell-mediated assays have been developed to define the system with the greatest ability to predict clinical responses. The humoral assay include the immune adherence, membrane immunofluorescence, FACS analysis, ELISA, and radioimmunoassays.

For example, the present inventors have demonstrated that serum from cancer patients and normal healthy donors contained IgM and IgG antibodies reactive to the peptide QDLTMKYQIF, SEQ ID NO:1, and to the peptide KYQI, SEQ ID NO:8. Therefore, the peptides can be used to induce a humoral immune response in addition to the CTL response discussed herein. The 10 amino acid peptide, SEQ ID NO:1, has also been found to induce delayed type hypersensitivity. Melanoma patients were injected with 10 µg of the peptide intradermally and DTH responses were observed. Of 25 patients tested, 10 showed a positive response. Hence, the 10 amino acid peptide, SEQ ID NO:1, is useful as a skin test antigen to monitor immune responses against the antigen and to aid in prognosis of the disease.

In light of the present disclosure therefore, the synthetic peptide antigens may be used to establish more accurate serologic assay systems and skin tests that have the ability to predict immune and clinical responses induced by these newly discovered antigens.

EXAMPLE XI

Use of the cDNA to Isolate the Full Length Gene

Full-length peptide analysis of the antigenic protein is important in order to determine the location of the antigen epitope, to search other sites for cross reactive antigens within the 43 kD protein, and to evaluate its biological function and pathogenic significance for the disease. The sequence of the cloned cDNA #810 is useful as a primer or a probe to isolate the full length gene encoding the 43 kD protein. The techniques to accomplish the isolation of the full length gene are well known in the art.

For example, a genomic library could be constructed by well known techniques and screened with the cDNA clone #810. The library would be separated, for example by polyacrylamide gel electrophoresis, or agarose gel electrophoresis and then transferred to a filter such as a nitrocellulose filter. The clone #810 would then be labeled with $^{32}P$ by enzymatic labelling with polynucleotide kinase, for example. The clone could also be radioactively labeled by nick translation or in a polymerase chain reaction that included radiolabeled nucleotides. Alternatively, the probe could be labeled with a fluorescent marker such as biotin or any fluorophore. Such labelling techniques are well known in the art.

The labeled probe would then be hybridized to the denatured DNA on the filter and washed under increasingly stringent conditions, incrementally higher temperatures for example, until the positive clones can be identified by autoradiography or by fluorescence. These positive clones would then be rescreened and sequenced to determine the full gene sequence encoding the 431 kD protein.

The full protein could then be expressed in an *E. coli* strain, for example, and used for further analysis. It is understood that the protein could also be truncated or altered by site directed mutagenesis, for example and that such altered proteins or partial sequences would also fall within the scope of the present invention.

EXAMPLE XII

CTL Response To the Antigen

Cytotoxicity Assays

A standard $^{51}Cr$ release assay was performed as previously described (Hayashi et al., 1992). Melanoma cell lines were harvested and labeled with 100 $\mu Ci^{51}Cr$ (Amersham, Arlington Heights, Ill.) for 2 h at 37° C. and used as targets. The labeled targets were washed and resuspended in culture medium and seeded in round-bottom 96 well microtiter plates at $5 \times 10^3$ cells/well and then effector cells were added. All assays (200 µl/well) were carried out in triplicate. After 6 h of incubation, 100 µl of supernatants were collected and counted. % specific cytolysis was calculated as follows: % specific cytolysis=100×(experimental release-spontaneous release/5% Triton X release-spontaneous release).

For peptide experiments, BCL were pulsed with a peptide at 10 μM, simultaneously labeled with 100 μCi$^{51}$Cr for 2 h at 37° C. and were used as targets. 17% lysis was set as the threshold for defining a positive or negative response at an E:T of 80:1. This value was selected because it was 3SD above the mean lysis obtained from two negative controls: PBMC from 19 control normal donors tested on autologous BCL pulsed with peptide #810, SEQ ID NO:1, (3SD above mean=16.9%); and PBMC from 19 melanoma patients tested on autologous BCL with medium only or pulsed with an irrelevant decapeptide (3SD above mean=16.5%).

Representative data of 19 patients and 19 control normal donors are shown in FIG. 9A. At 0, 4 and 8 weeks, a patient's PBMC show positive cytolyses (≧17% at E:T of 80:1) of autologous #810, SEQ ID NO:1—pulsed BCL while those of a normal donor do not. Lysis of autologous BCL without peptides did not exceed 7% by any effector. Mean cpm±SD of triplicate cultures are shown in FIG. 9B. At 4 and 8 weeks, values of the patient's PBMC with #810, SEQ ID NO:1 peptide 0.001–20 μM are significantly higher than hose without #810, SEQ ID NO:1 (p<0.005) and maximal SIs were 2.71 and 2.87 at 4 and 8 weeks respectively, whereas significant proliferative response to #810, SEQ ID NO:1 is not observed before vaccination (0 weeks) and in a control donor.

Proliferation Assays

PBMC (1×10$^5$ cells/well) were seeded into 96-well plates and peptides were added at desired concentrations in a total 200 μl/well of culture medium. Tritiated thymidine ([$^3$H]TdR) (0.5 μCi/well, Amersham Arlington Heights, Ill.) was added during the last 18 h of a 4 day culture period. Cultures were set up in triplicate and harvested with a Brandel cell harvester and then counted in a Beckman scintillation counter. Stimulation index (SI) was calculated as follows: [mean cpm of triplicate cultures with peptide]\mean cpm without peptide]. Maximal SI among various concentrations ≧2.0 was defined as a positive response to peptide #810, SEQ ID NO:1 because it was 3SD above the mean of maximal SI obtained from two negative controls: PBMC from 19 control donors tested on #810, SEQ ID NO:1 (3SD above mean=1.97); and PBMC from 19 melanoma patients tested on an irrelevant decapeptide (3SD above mean=1.37).

PBMC from vaccinated melanoma patients were assayed for peptide #810 recognition and the results were compared among various phases (0, 4, 8w) and also compared with those of control normal donors. In sixteen of 19 melanoma patients (84.2%), PBMC recognized and lysed autologous BCL pulsed with #810 peptide, SEQ ID NO:1, either before or after vaccination while PBMC from only two of 19 normal donors (10.5%) showed such cytotoxicity (Table 2, FIG. 9A). This cytotoxicity was specific to #810, SEQ ID NO:1, since PBMC from patients and normal donors failed to lyse autologous BCL without peptides or pulsed with a decapeptide of irrelevant amino-acid sequence. Such #810, SEQ ID NO:1—specific cytotoxicity of melanoma patients was significantly increased after vaccination in 15 patients (78.9%). In most cases that activity was the highest at 4 weeks and rather reduced at 8 weeks, however, it was still above the prevaccination level.

PBMC from melanoma patients also showed proliferative response to #810, SEQ ID NO:1 although the magnitude of response was weaker than that of cytotoxicity assays (FIG. 9B). In 13 patients (68.4%), [$^3$H]TdR uptake of peptide-stimulated PBMC was increased more than two-fold over those without #810, SEQ ID NO:1, and such proliferative response was significantly enhanced after vaccination in 12 patients (63.2%). That response was also specific to #810, SEQ ID NO:1 since that was not observed when a patient's PBMC were incubated with an irrelevant decapeptide.

Those results suggest that PBMC only from melanoma patients may be latently sensitized in vivo with #810, SEQ ID NO:1, even before vaccination and cellular immune responses to this peptide may be recalled in vitro, indicating that autologous melanoma cells may specifically present #810, SEQ ID NO:1. The augmentative effect of vaccination suggests that allogeneic melanoma cells of MCV may also present #810, SEQ ID NO:1, to patients' lymphocyte and enhance specific responses to this peptide. In contrast, PBMC of normal donors may not be in vivo sensitized with #810, SEQ ID NO:1, though it does commonly exist in being somatic cells.

EXAMPLE XIII

Effect of in vitro Restimulation with Peptide of SEQ ID NO:1

PBMC (3×10$^6$/well) from melanoma patients 4 weeks after MCV immunization were stimulated with #810 peptide, SEQ ID NO:1, at 10 μM in 2ml culture medium in 24-well plates at 37° C. After 5 days of incubation, cells were harvested and assayed for cytotoxicity.

PBMC from patient A 4 weeks after vaccination were in vitro restimulated with #810, SEQ ID NO:1, and were assayed for cytolyses of autologous #810, SEQ ID NO:1—pulsed BCL and melanoma MA targets (FIG. 10). □ and ○ indicate cytotoxicity of control PBMC cultured with medium only. Lysis of autologous BCL without peptides or pulsed with an irrelevant decapeptide did not exceed 8% at an E:T of 80:1 by either effector. Lysis of K562 by #810, SEQ ID NO:1—restimulated PBMC and control at E:T of 80:1 were 24.0 and 24.5%, respectively. Data are representative of three separate experiments.

Cold Target Inhibition Assays

Unlabeled cold target cells (50 μl) were seeded in 96-well plates at appropriate concentrations. Effector cells (100 μl) were added into the well and incubated for 1 h at 37° C. before the addition of $^{51}$Cr-labeled hot targets at desired cold:hot target ratios.

TABLE 2

Summary of peptide #810-specific cytotoxicity and proliferative response of PBMC from vaccinated melanoma patients.

|  | cytotoxicity[a] | | proliferative response[b] | |
| --- | --- | --- | --- | --- |
|  | mean ± SD of % lysis (E:T = 80:1) | positive response (%) | mean ± SD of maximal SI | positive response (%) |
| vaccinated melanoma patients[c] (n = 19) | 0 w 19.85 ± 4.80[d] | 13 (68.4) | 1.62 ± 0.31[d] | 3 (15.8) |
|  | 4 w 40.25 ± 9.13[d,e] | 15 (78.9) | 2.43 ± 0.55[d,e] | 12 (63.2) |
|  | 8 w 38.70 ± 8.76[d,e] | 16 (84.2) | 2.50 ± 0.60[d,e] | 13 (68.4) |
|  | positive response either pre or post vaccination | 16 (84.2) |  | 13 (68.4) |
|  | enhanced response[f] post vaccination | 15 (78.9) |  | 12 (63.2) |
| control (n = 19) | 6.10 ± 3.60 | 2 (10.5) | 0.98 ± 0.33 | 0 (0) |

[a,b]Cytotoxicity against autologous BCL pulsed with #810 and proliferative response to #810 were evaluated as described above.
[c]Melanoma patients were immunized with MCV and were tested before (0 w) and at monthly intervals (4, 8 w) after the initiation of vaccination.
[d]Significant difference vs values of control (p < 0.005).
[e]Significant difference vs values of 0 w (p < 0.005).
[f]Number and % of patients are shown whose responses to peptide #810 were significantly increased either at 4 or 8 w compared to 0 w (p0.05).

PBMC from patient A were restimulated with #810, SEQ ID NO:1 similarly to FIG. 10 and assayed for cytolyses of autologous $^{51}$Cr-labeled #810, SEQ ID NO:1—pulsed BCL (FIG. 11A) and melanoma MA (FIG. 11B) at E:T of 20:1. Unlabeled cold target cells were added at indicated ratios. Lysis of BL without peptides was 3.0% at E:T of 20:1. Data are representative of four separate experiments.

810, SEQ ID NO:1—restimulated PBMC from vaccinated patient A revealed more than a 3-fold increase in cytotoxicity against autologous #810, SEQ ID NO:1— pulsed BCL (67.3%, E:T=40:1) compared to a control cultured without peptide (18.0%) (FIG. 10). Such cytotoxicity was #810, SEQ ID NO:1— specific and different from non-specific lymphokine-activated killer (LAK) activity since killing activity against K562 (LAK target) or autologous BCL without peptides or pulsed with an irrelevant decapeptide was not increased. Furthermore, this #810, SEQ ID NO:1—restimulation simultaneously enhanced killing activity against autologous melanoma cells. These results indicate that the identical #810 antigen, SEQ ID NO:1, may possibly be presented on the surface of autologous melanoma cells similarly to #810, SEQ ID NO:1—pulsed BCL. That possibility was explored by cold-target inhibition tests. Cold autologous melanoma cells inhibited lysis of autologous #810, SEQ ID NO:1—pulsed BCL, although less efficiently than unlabeled #810, SEQ ID NO:1—pulsed BCL (FIG. 11A). Conversely autologous #810, SEQ ID NO:1—pulsed BCL completely blocked lysis of autologous melanomas FIG. 11B). These data indicate that #810 antigen, SEQ ID NO:1, may be presented on the surface of melanoma cells and can be recognized as a target antigen of cytolysis.

Antibody Inhibition Assays

810, SEQ ID NO:1—restimulated PBMC from patient A were assayed for cytolyses of autologous #810, SEQ ID NO:1—pulsed BCL and melanoma MA at E:T of 40:1 in the presence or absence of antibodies. A final concentration of each antibody was 10 µg/ml. Lyses of autologous BCL without peptides and pulsed with an irrelevant decapeptide were 5.4 and 5.2%, respectively. Data are representative of four separate experiments.

EXAMPLE XIV

HLA Restriction of Peptide-Specific CTL

HLA Typing

To identify the class I determinants that restrict the recognition of peptide #810, SEQ ID NO:1, a series of HLA-typed melanoma patients were tested (Table 3). PBMC from patients were used for HLA typing by a complement-mediated microcytotoxicity assay in Dr. Paul Terasaki's laboratory (UCLA School of Medicine, Los Angeles, Calif.).

Restriction of Recognition

As it has often been demonstrated that HLA-A antigens are important restrictive elements for CTL recognition of melanomas (Kawakami et al., 1992), HLA-A epitopes among class I antigens were selected. In HLA-A2+ patients, A, B and C, in vitro restimulation with #810, SEQ ID NO:1, succeeded in the enhancement of CTL activity against both autologous #810, SEQ ID NO:1—pulsed BCL and melanoma targets. By contrast, #810, SEQ ID NO:1— restimulated PBMC from A2(–) patient G did not show such CTL activity though this patient shared A29 with patient B. These suggest HLA-A2 may serve as a restricting element for #810, SEQ ID NO:1 recognition. Among A2(–) patients, #810, SEQ ID NO:1—restimulated PBMC from patient D (A11, 30) and E (A28, 31) appeared to recognize #810, SEQ ID NO:1, while those from patient F (A24,–), G (A29,–) and H (A24, 32) did not. HLA-B antigens did not appear to play a significant role in #810, SEQ ID NO:1—recognition; #810, SEQ ID NO:1n—restimulated PBMC from patient A (HLA-B7+) and patient B (B44+) recognized peptide #810, SEQ ID NO:1, while those from patient H (B7&44+) did not. The present results indicate that A2 and A11 may function as such restricting elements for #810, SEQ ID NO:1, recognition in patient A–D while A24 may not (patient F and H).

To verify this possibility, #810, SEQ ID NO:1— restimulated PBMC from patient B (A2+) and D (A11+) were tested for cytolyses of autologous and allogeneic HLA-A-matched or mismatched BCL pulsed with #810, SEQ ID NO:1 (FIG. 13). #810, SEQ ID NO:1—restimulated PBMC from A2+ patient B could lyse allogeneic A2+ BCL pulsed with #810, SEQ ID NO:1, whereas they failed to lyse A2(–) targets. Similarly #810, SEQ ID NO:1—restimulated PBMC from A11+ patient D could only lyse A11+ BCL pulsed with #810, SEQ ID NO:1. BCL targets without #810, SEQ ID NO:1 were not lysed by those effectors, indicating that the lysis was peptide-specific and not allo-reactive. These results suggest that HLA-A2 and A11 can serve as restricting elements for #810, SEQ ID NO: 1, recognition. Such restriction was further evaluated against HLA-matched or mismatched melanoma targets (Table 4). In A2+ patients (A, B), #810, SEQ ID NO:1—restimulation enhanced the cytotoxicity against A2+ melanoma targets while such enhancement was not observed against A2(–) melanoma targets. Similar results were obtained in A11 + patient D. Those results suggest that melanomas may present #810 antigen, SEQ ID NO:1, to CTL in association with class I molecules, at least with HLA-A2 and A11, and also indicate that #810, SEQ ID NO:1, may function as a CTL epitope of melanoma.

TABLE 3

HLA restriction of peptide recognition by #810, SEQ ID NO:1 -restimulated PBMC.

| | | | % specific cytolysis[a] vs | | | |
|---|---|---|---|---|---|---|
| | HLA | | autologous #810-pulsed | | autologous | |
| patients | A | B | BCL | | melanoma | |
| A | 2,3 | 7,8 | 64.3 | (18.0) | 55.1 | (5.4) |
| B | 2,29 | 44,— | 25.9 | (13.5) | 17.4 | (5.9) |
| C | 2,28 | 27,58 | 31.8 | (14.9) | 24.1 | (3.2) |
| D | 11,30 | 18,70 | 29.7 | (19.0) | 37.5 | (9.6) |
| E | 28,31 | 39,60 | 30.3 | (21.4) | 12.0 | (8.0) |
| F | 24,— | 48,53 | 11.0 | (10.0) | 3.0 | (3.0) |
| G | 29,— | 49,— | 3.4 | (7.2) | 3.0 | (4.0) |
| H | 24,32 | 7,44 | 0 | (0) | 11.0 | (10.4) |

[a]PBMC from vaccinated patients were restimulated in vitro with or without peptide #810, SEQ ID NO:1, for 5d and were analyzed for cytotoxicity at E:T of 40:1. Values in parentheses indicate cytotoxicity of control PBMC cultured without peptide. Lysis of autologous BCL without peptides or pulsed with an irrelevant decapeptide did not exceed 7% at this ratio by any effector. Data of each patient are representative of at least three separate experiments.

TABLE 4

Cytotoxicity of #810, SEQ ID NO:1 - restimulated PBMC[a]
against autologous and allogeneic melanoma targets.

| Target<br>HLA-A | M10<br>24,33 | M24<br>11,33 | M101<br>2,29 | MA<br>2,3 | MB<br>2,29 | MD<br>11,30 | MN<br>1,2 | MP<br>2,9 | K562<br>-) |
|---|---|---|---|---|---|---|---|---|---|
| patient A[b] control | 9.8 | 9.1 | 8.6 | 5.4 | 9.5 | 3.0 | 6.4 | 7.4 | 15.1 |
| HLAA2,3 #810 | 9.3 | 1.6 | 37.8 | 55.1 | 23.6 | 4.0 | 20.2 | 18.0 | 16.0 |
| patient B control | 8.2 | 11.6 | 9.1 | 8.6 | 5.9 | 6.0 | 9.5 | 11.1 | 15.7 |
| HLAA2,29 #810 | 9.2 | 11.9 | 35.1 | 31.4 | 17.4 | 7.0 | 16.1 | 31.7 | 14.6 |
| patient D control | 8.2 | 9.0 | 3.1 | 11.7 | 4.9 | 9.6 | 6.3 | 8.7 | 17.7 |
| HLAA11,30 #810 | 7.1 | 37.4 | 2.0 | 8.0 | 5.0 | 37.5 | 6.9 | 9.8 | 16.1 |

[a]PBMC from vaccinated patients were restimulated in vitro with or without peptide #810, SEQ ID NO:1, for 5 d and were analyzed for cytotoxicity against a variety of melanoma targets at E:T of 40:1. Parentheses indicate HLA-A typing of a target or effector. Underlined results denote autologous or allogeneic melanoma targets sharing HLA-A antigens with effectors. Cytotoxicity against K562 was tested as a negative control. Data of each patient are representative of four separate experiments.
[b]Patient A, B, D are bearers of melanoma MA, MB, MD, respectively.

Representative data of three experiments are shown as % specific cytolysis at E:T of 40:1 against #810, SEQ ID NO:1—pulsed BCL targets in FIG. 13. Effectors are #810, SEQ ID NO:1—restimulated PBMC of patient B (HLA-A2+) and D (HLA-A-11+). Parentheses of left margin indicate HLA-A or B antigens shared between the effectors and targets. Each autologous and allogeneic target was also preincubated in media only or pulsed with an irrelevant decapeptide, and was tested for lysis by the effectors. Lysis of those control targets did not exceed 5% by either effector.

EXAMPLE XV

Effect of L92 on Cytolysis by #810, SEQ ID NO:1-Induced CTL

An attempt was made to block both autologous #810, SEQ ID NO:1—pulsed BCL and melanoma killing by monoclonal antibody L92, directed against #810, SEQ ID NO:1. Although this antibody showed specific binding activity to #810, SEQ ID NO:1, in a solid-phase peptide enzyme-linked immunosorbent assay (ELISA), it could neither bind substantially to a #810, SEQ ID NO:1—pulsed BCL nor melanomas of patient A in IA assays Cable 5). Similar results were obtained in flow cytometries using L92. This antibody also exhibited only slight inhibition of CTL lyses of both targets and inhibitory effect was not changed when antibody concentration was increased up to 50 μg/ml. Thus antibody L92 could not detect #810 antigen, SEQ ID NO:1, on the surface of target cells although that antigenic epitope appeared to be associated with class I molecules and recognized by CTL.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 5

Inhibition of autologous #810, SEQ ID NO:1 -pulsed BCL and melanoma lyses by monoclonal antibody to #810 peptide.

| | Target Cells | | | |
|---|---|---|---|---|
| | autologous<br>#810-pulsed BCL | | autologous<br>melanoma (MA) | |
| Treatment[a] | IL assay[b] | %<br>lysis[c] | IA<br>assay | %<br>lysis |
| control | | 67.3 | | 58.2 |
| L92 (anti-#810) | ± | 54.4 | — | 43.6 |
| L612 (anti-GM$_3$) | ND[d] | 65.3 | ND | 54.3 |
| anti-class I | ND | 5.2 | ND | 8.0 |

[a]Target cells were premcubated for 1 h with or without monoclonal antibodies before the addition of effector cells. A final concentration of each antibody in a 6 h-cytotoxicity assay was 10 μg/ml. L612 and anticlass I antibodies were used as a negative and positive control, respectively.
[b]IA assays were performed against those targets as described above.
[c]Effector cells were #810, SEQ ID NO:1 -restimulated PBMC from vaccinated patient A (HLA-A2,3); E:T=40:1. Lysis of autologous BCL without peptides or pulsed with an irrelevant decapeptide did not exeeed 8%. Data are representative of three separate experiments.
[d]Not done.

REFERENCES

The following references, to the extent that they provide exemplary procedural or other details supplementary to those set forth herein, are specifically incorporated herein by reference.

Amagai M, Klaus-Kovtum V, Standly J R. Autoantibodies against novel epithelial cadherin in pemphigus vulgaris, a disease of cell adhesion. *Cell* 67:869–877, 1991.

Brown J P, Hewick R M, Hellström I, Hellstrom K E, Doolittle R F, Dreyer W J. Human melanoma-associated antigen p97 is structurally and functionally related to transferrin. *Nature* 296: 171–173, 1982.

Brown, J P, Nishiyama K, Hellstrom I, Hellstrom K E. Structural characterization of human melanoma-associated antigen p97 in normal and neoplastic tissues. *J Immunol* 127:539–546, 1981.

Cahan L D, Irie R F, Singh R, Cassidenti A, Pauluson J C. Identification of a human neuroectodermal tumor antigen (OFA-I-2) as ganglioside GD2. *Proc Natl Acad Sci USA* 79:7629–7633, 1982.

Carey T E, Lloyd K O, Takahashi T, Travassos L R, Old L J. AU cell-surface antigen of human malignant melanoma.

Solubilization and partial characterization. *Proc Natl Acad Sci USA* 76:2898, 1979.

Challopadhyay P, Kaveri S-V, Byars N, Starkey J, Ferrone S. Human high molecular weight melanoma-associated antigen mimicry by an anti-idiotypic antibody: Characterization of the immunogenicity of the immune response to the mouse monoclonal antibody IMel-1. *Cancer Res* 51:6045–6051, 1991.

Cheresh D A, Resifeld R A, Varki A P. O-acetylation of disialoganglioside GD3 gy human melanoma cells creates a unique antigenic determinant. *Science* 225:844–846, 1984.

Cheresh D A, Varki A P, Varki N M, Stallcup W B, Levine J, Reisfeld R A. A monoclonal antibody recognizes an O-acetylated sialic acid in a human melanoma-associated ganglioside. *J Biol Chem* 259:7453–7459, 1984.

Chirgwin, J M, Przybyla, A E, McDonald R J, Rutter, W J. Isolation of biologically active ribonucleic acid from sources enriched in ribonuclease. *Biochem* 18:5294–5299, 1979.

Dropcho E J, Chen Y-T, Posner J B, Old L J. Cloning of a brain protein identified by autoantibodies from a patient with paraneoplastic cerebellar degeneration. *Proc Natl Acad Sci, USA* 84:4552–4556, 1987.

Erb K, Ditzel H, Wæver-Rassmussen J. Borup-Christensen P, Jensenius J C. Antigens recognized by two human monoclonal IgM anti-colon cancer antibodies, 16.88 and C-OU1 (B9165). *Hum Antibod Hybridomas* 2:215–221, 1991.

Euhus D M, Gupta R K, Morton D L. Association between allo-immunoreactive and xeno-immunoreactive subunits of a glycoprotein tumor-associated antigen. *Cancer Immunol Immunother* 32:214–220, 1990.

Fontan E, Skalani-Jusforgues H, Fauve R M. Immunostimulatory human urinary protein. *Proc Natl Acad Sci USA* 89:4358–4362, 1992.

Fontan E, Skalani H. Fauve R M. Macrophage-induced cytotoxicity and anti-metastatic activity of a 43-kDa human urinary protein against the Lewis tumor. *Int J Cancer* 53:131–136, 1993.

Hayashi Y, Hoon D S B, Park M S, Terasaki P I, Foshag L J and Morton D L. Induction of CD4+ cytotoxic T cells by sensitization with allogeneic melanomas bearing shared or cross-reactive HLA-A. *Cell Immunol* 139:411–424, 1992.

S Hayashibe K, Mishima Y, Ferrone S. Cloning and in vitro expression of a melanoma-associated antigen immunogenic in patients with melanoma. *J Immunol* 147:1098–1104, 1991.

Hellstrom I, Hellstrom K. Melanoma vaccines—why and how. IN *Cutaneous Melanoma,* C M Balch, A N Houghton, G W Milton, Sober A J, and S-J Song (Pub), J. B. Lippincott, P A, pp. 542–546, 1992.

Houghton A N, Brooks H, Cote R J, Taormina M C, Oettgen H F, Old L J. Detection of cell surface and intracellular antigens by human monoclonal antibodies. *J Exp Med* 158:53–65, 1983.

Irie R F, Sze L L, Saxton R E. Human antibody to OFA-1, a tumor antigen, produced in vitro by EBV-transformed human B-lymphoblastoid cell lines. *Proc Natl Acad Sci USA* 79:5666–5670, 1982.

Irie R F, Jones P C, Morton D L, Sidell N. In vitro production of human antibody to a tumor-associated fetal antigen. *Brit J Cancer* 44:262–266, 1981.

Irie R F, Irie K, Morton D L. A membrane antigen common to human cancer and fetal brain tissues. *Cancer Res* 36:3510–3517, 1976.

Kan-Mitchell J, Iman A, Kempf R, Taylor C R, Mitchell M S. Human monoclonal antibodies directed against melanoma tumor-associated antigens. *Cancer Res* 46:2490–2510, 1986.

Kawakami Y, Zakut R, Topalian S L, Stotter H and Rosenberg S A. Shared human melanoma antigens: recognition by tumor-infiltrating lymphocytes in HLA-A2.1-transfected melanomas. *J Immunol* 148:638–643, 1992.

Kusama M, Kageshita T, Chen Z J, Ferrone S. Characterization of syngeneic anti-idiotypic MAb to murine anti-human high molecular weight-melanoma-associated antigen (HMW-MAA). *J Immunol* 143:3844–3852, 1989.

Larrick L W, Gavilondo J V, Coloma M Y, Fry K E. Construction of recombinant therapeutic monoclonal antibodies. IN *Therapeutic Monoclonal Antibodies,* C A K Borrebaech and L W Larrick (eds), Stockton Press, New York, pp. 17–35, 1990.

Li J, Henn M, Oratz R, Bystryn J-C. The antibody response to immunization to a polyvalent melanoma antigen vaccine. *Clin Res* 38:660A, 1990.

Livingston P O, Natoli E L, Calves M J, Stockert E, Oettgen H F, Old L J. Vaccines containing purified GM2 ganglioside elicit GM2 antibodies in melanoma patients. *Proc Natl Acad Sci USA* 84:2911–2915, 1987.

Livingston P O. Immune responses to melanoma vaccines: Focus on gangliosides. *35th Annual Clinical Conference Proceedings,* M. D. Anderson Cancer Center, Houston, Tex., p. 72, 1991.

Livingston P O. Experimental and clinical studies with active specific immunotherapy. IN *Immunity to Cancer II,* M S Mitchell (ed), Alan R. Liss, New York, 1989.

Mittelman A, Chen, Z J, Yang H, Wong G Y, Ferrone S. Human high molecular weight melanoma-associated antigen HMW-MAA) mimicry by mouse anti-idiotype monoclonal antibody $MK_2$-23: Induction of humoral anti-HMW-MAA immunity and prolongation of survival in patients with Stage IV melanoma. *Proc Natl Acad Sci USA* 89:466–470, 1992.

Morisaki T, Yuzuki D H, Lin R T, Foshag L J, Morton D L and Hoon D S B. Interleukin 4 receptor expression and growth inhibition of gastric carcinoma cells by interleukin 4. *Cancer Res* 52:6059–6065, 1992.

Morton D L, Foshag L J, Hoon D S B, Nizze J A, Wanek L A, Chang C, Davtyan D G, Gupta R K, Elashoff R, Irie R F. Prolongation of survival in metastatic melanoma after active specific immunotherapy with a new polyvalent melanoma vaccine. *Ann Surg* 16(4):463–482, 1992.

Portoukalian J, Carrel S, DorèJ-F Rümke P. Humoral immune response in disease-free advanced melanoma patients after vaccination with melanoma-associated gangliosides. *Int J Cancer* 49:893–899, 1991.

Ravindranath M H, Morton D L, Irie R F. An epitope common to gangliosides O-acetylated GD3 and GD3 recognized by antibodies in melanoma patients after active specific immunotherapy. *Cancer Res* 49:3891–3897, 1989.

Real F X, Mattes J M, Houghton A N, Oettgen H F, Lloyd K O, Old L J. Class 1 (unique) antigens of human melanoma. Identification of a 90,000 dalton cell surface glycoprotein by autologous antibody. *J Exp. Med* 160:1219, 1984.

Reisfeld R A, Cheresh D A. Human tumor antigens. *Adv Immunol* 40:323–377, 1987.

Rosenberg S A, Spiess P and Lafreniere R. A new approach to the Adoptive Immunotherapy of Cancer with Tumor-Infiltrating Lymphocytes. *Science* 233:1318, 1986.

Smith L H, Yin A, Glasky M S, Tyler N, Robles M, Foster C A, Bieber M, Teng NNH. Human monoclonal antibody recognizing an antigen associated with ovarian and other adenocarcinomas. *Am J Obstet Gynecol* 166:634–645, 1992.

Szabo A. Dalmau J, Manley G, Rosenfeld M, Wong E, Henson J, Posner J B, Furneaux H M. HVD, a paraneoplastic encephalomyelitis antigen, contains RNA-binding domains and is homologous to Elav and Sex-lethal. *Cell* 67:325–333, 1991.

Tai T, Cahan L D, Paulson J C, Saxton R E,, Morton D L, Irie R F. Enzyme linked immunosorbent assay (ELISA) for the detection of human antibody to ganglioside GD2. *J Natl Cancer Inst* 73:627–633, 1984.

Tai T, Paulson J C, Cahan L D, Irie R F. Ganglioside GM2 as a human tumor antigen (OFA-1-I). *Proc Natl Acad Sci USA* 80:5392–5396, 1983.

Tai T, Cahan L D, Tsuchida T, Saxton R E, Irie R F, Morton D L. Immunogenicity of melanoma-associated gangliosides in cancer patients. *Int J Cancer* 35:607–612, 1985.

Tan E M. Autoantibodies in pathology and cell biology. *Cell* 67:841–842, 1991.

Vlock D R, Scalise D, Meglin N, Kirkwood J M, Ballou B. Isolation and partial characterization of melanoma-associated antigens identified by autologous antibody. *J Clin Invest* 81:1746–1751, 1988.

Watanabe T, Pukel C S, Takeyama H, Lloyd K O, Shiku H, Li L T C, Travassos L R, Oettgen H F, Old L J. Human melanoma antigen AH is an autoantigenic ganglioside related to GD2. *J Exp Med* 156:1884–1889, 1982.

Woodbury R G, Brown J P, Yeh M R, Hellstrom I, Hellstrom K E. Identification of a cell surface protein, p97, in human melanomas and certain other neoplasms. *Proc Natl Acad Sci USA* 77:2183–2186, 1980.

Yamamoto S, Hoon D S B, Chandler P, Schmid I, Irie R F. Generation of lymphokine-activated killer cell activity by low-dose recombinant interleukin-2 and tumor cells. *Cellular Immunol* 128:516–527, 1990.

Yamamoto S, Yamamoto T, Saxton R E, Hoon D S B, Irie R F. Anti-idiotype monoclonal antibody carrying the internal image of ganglioside GM3. *J Natl Cancer Inst* 82:1757–1760, 1990.

What is claimed is:

1. A method of treating a human cancer patient comprising administering to said patient a composition comprising a purified polypeptide comprising an amino acid sequence KYQI (SEQ ID NO:8).

2. The method of claim 1, wherein said polypeptide comprises an amino acid sequence QDLTMKYQI (SEQ ID NO:9).

3. The method of claim 2, wherein said polypeptide comprises an amino acid sequence QDLTMKYQIF (SEQ ID NO:1).

4. The method of claim 1, wherein said polypeptide is further defined as comprising a molecular mass of about 43 kDa.

5. The method of claim 1, wherein said polypeptide is further defined as having a length of less than 100 amino acids.

6. The method of claim 5, wherein said polypeptide is further defined as having a length of less than 50 amino acids.

7. The method of claim 6, wherein said polypeptide is further defined as having a length of less than 25 amino acids.

8. The method of claim 7, wherein said polypeptide is further defined as having a length of 10 amino acids or less.

9. The method of claim 1, wherein said polypeptide exhibits immunoreactivity with monoclonal antibody L92.

10. The method of claim 9, wherein said composition comprises an amount of a polypeptide effective to elicit a CTL or antibody response.

11. The method of claim 1, wherein said composition comprises a vaccine.

12. The antigen composition of claim 11, wherein said polypeptide is a component of a polyvalent melanoma cell vaccine.

13. The method of claim 1, wherein the polypeptide is present in said composition at a concentration of between 1 mg/ml and about 10 mg/ml.

14. The method of claim 13, wherein the polypeptide is present in said composition at a concentration of about 5 mg/ml.

15. The method of claim 1, wherein said polypeptide is coupled or conjugated with a carrier.

16. The method of claim 1, wherein said vaccine comprises an adjuvant, an excipient, an auxiliary substance or a salt.

17. The method of claim 1, wherein said administration is an injection.

18. The method of claim 1, further comprising the administration of a melanoma cell vaccine.

19. The method of claim 1, further comprising subsequent administrations of said composition.

20. The method of claim 1, wherein said human cancer patient is a human melanoma patient.

21. A method of treating a human cancer patient comprising, administering to said patient a composition comprising a purified polypeptide comprising an amino acid sequence QDLTMKYQI (SEQ ID NO:9).

22. The method of claim 21, wherein said polypeptide comprises an amino acid sequence QDLTMKYQIF (SEQ ID NO:1).

23. The method of claim 21, wherein said polypeptide is further defined as comprising a molecular mass of about 43 kDa.

24. The method of claim 21, wherein said polypeptide is further defined as having a length of less than 100 amino acids.

25. The method of claim 24, wherein said polypeptide is further defined as having a length of less than 50 amino acids.

26. The method of claim 25, wherein said polypeptide is further defined as having a length of less than 25 amino acids.

27. The method of claim 26, wherein said polypeptide is further defined as having a length of 10 amino acids or less.

28. The method of claim 21, wherein said polypeptide exhibits immunoreactivity with monoclonal antibody L92.

29. The method of claim 28, wherein said composition comprises an amount of a polypeptide effective to elicit a CTL or antibody response.

30. The method of claim 21, wherein said composition comprises a vaccine.

31. The antigen composition of claim 30, wherein said polypeptide is a component of a polyvalent melanoma cell vaccine.

32. The method of claim 21, wherein the polypeptide is present in said composition at a concentration of between 1 mg/ml and about 10 mg/ml.

33. The method of claim 32, wherein the polypeptide is present in said composition at a concentration of about 5 mg/ml.

34. The method of claim 21, wherein said polypeptide is coupled or conjugated with a carrier.

35. The method of claim 30, wherein said vaccine comprises an adjuvant, an excipient, an auxiliary substance or a salt.

36. The method of claim 21, wherein said administration is an injection.

37. The method of claim 21, further comprising the administration of a melanoma cell vaccine.

38. The method of claim 21, further comprising subsequent administrations of said composition.

39. The method of claim 21, wherein said human cancer patient is a human melanoma patient.

40. A method of treating a human cancer patient comprising, administering to said patient a composition comprising a purified polypeptide comprising an amino acid sequence QDLTMKYQIF (SEQ ID NO:1).

41. The method of claim 40, wherein said polypeptide exhibits immunoreactivity with monoclonal antibody L92.

42. The method of claim 40, wherein said composition comprises a vaccine.

43. The antigen composition of claim 42, wherein said polypeptide is a component of a polyvalent melanoma cell vaccine.

44. The method of claim 42, wherein said composition induces anti-tumor humoral or cell-mediated immune responses.

45. The method of claim 40, wherein said human cancer patient is a human melanoma patient.

* * * * *

```
                       SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 10 amino acids
          (B) TYPE: amino acid
          (C) STRANDEDNESS:
          (D) TOPOLOGY: linear (xi) SEQUENCE DESCRIPTION: SEQ ID NO:1:

Gln Asp Leu Thr Met Lys Tyr Gln Ile Phe
1               5                   10

(2) INFORMATION FOR SEQ ID NO:2:

(i) SEQUENCE CHARACTERISTICS:
          (A) LENGTH: 14 amino acids
          (B) TYPE: amino acid
          (C) STRANDEDNESS:
          (D) TOPOLOGY: linear (xi) SEQUENCE DESCRIPTION: SEQ ID NO:2:

Asp Ser Arg Pro Gln Asp Leu Thr Met Lys Tyr Gln Ile Phe
1               5                   10

(2) INFORMATION FOR SEQ ID NO:3:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (xi) SEQUENCE DESCRIPTION: SEQ ID NO:3:

AAAGATCTGA TATTTCATAG TCAGATCCTG                                    30

(2) INFORMATION FOR SEQ ID NO:4:

(i) SEQUENCE CHARACTERISTICS:
          (A) LENGTH: 27 base pairs
          (B) TYPE: nucleic acid
```

(C) STRANDEDNESS: single
            (D) TOPOLOGY: linear (xi) SEQUENCE DESCRIPTION: SEQ ID NO:4:

GACGACGAGC GCGGCGATAT CATCATC                                                    27

(2) INFORMATION FOR SEQ ID NO:5:

(i) SEQUENCE CHARACTERISTICS:
            (A) LENGTH: 10 amino acids
            (B) TYPE: amino acid
            (C) STRANDEDNESS:
            (D) TOPOLOGY: linear (xi) SEQUENCE DESCRIPTION: SEQ ID NO:5:

Ile Met Thr Gln Leu Phe Gln Asp Tyr Lys
1               5                   10

(2) INFORMATION FOR SEQ ID NO:6:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (xi) SEQUENCE DESCRIPTION: SEQ ID NO:6:

GATTCGCGCC CGCAGGATCT GACTATGAAA TATCAGATCT TTTAA                                 45

(2) INFORMATION FOR SEQ ID NO:7:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (xi) SEQUENCE DESCRIPTION: SEQ ID NO:7:

TTAAAAGATC AGATATTTCA TAGTCAGATC CTGCGGCCGC GAATC                                 45

(2) INFORMATION FOR SEQ ID NO:8:

(i) SEQUENCE CHARACTERISTICS:
            (A) LENGTH: 4 amino acids
            (B) TYPE: amino acid
            (C) STRANDEDNESS:
            (D) TOPOLOGY: linear (xi) SEQUENCE DESCRIPTION: SEQ ID NO:8:

Lys Tyr Gln Ile
1

(2) INFORMATION FOR SEQ ID NO:9:

(i) SEQUENCE CHARACTERISTICS:
            (A) LENGTH: 9 amino acids
            (B) TYPE: amino acid
            (C) STRANDEDNESS:
            (D) TOPOLOGY: linear (xi) SEQUENCE DESCRIPTION: SEQ ID NO:9:

Gln Asp Leu Thr Met Lys Tyr Gln Ile
1               5